(12) United States Patent
Failli et al.

(10) Patent No.: US 6,235,900 B1
(45) Date of Patent: May 22, 2001

(54) TRICYCLIC PYRIDINE N-OXIDES VASOPRESSIN AGONISTS

(75) Inventors: Amedeo A. Failli, Princeton Junction; Jay S. Shumsky, Hightstown; Eugene J. Trybulski, Princeton Junction, all of NJ (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/494,929

(22) Filed: Feb. 1, 2000

Related U.S. Application Data

(60) Provisional application No. 60/155,195, filed on Feb. 4, 1999.

(51) Int. Cl.$^7$ ..................... C07D 223/18; C07D 243/10; A61K 31/551
(52) U.S. Cl. ............. 540/586; 504/603; 504/575; 514/220; 514/211.08
(58) Field of Search .................. 514/220, 211.09; 540/586, 603, 575

(56) References Cited

U.S. PATENT DOCUMENTS

| | | | |
|---|---|---|---|
| 4,766,108 | 8/1988 | Ali | 514/16 |
| 5,055,448 | 10/1991 | Manning et al. | 514/16 |
| 5,070,187 | 12/1991 | Gavras et al. | 530/315 |
| 5,512,563 | 4/1996 | Albright et al. | 514/217 |
| 5,516,774 | 5/1996 | Albright et al. | 514/220 |
| 5,521,173 | 5/1996 | Venkatesan et al. | 214/220 |
| 5,532,235 | 7/1996 | Albright et al. | 514/215 |
| 5,536,718 | 7/1996 | Albright et al. | 514/220 |
| 5,610,156 | 3/1997 | Albright et al. | 514/220 |
| 5,612,334 | 3/1997 | Albright et al. | 514/220 |
| 5,624,923 | 4/1997 | Albright et al. | 514/220 |
| 5,654,297 | 8/1997 | Albright et al. | 514/215 |
| 5,686,445 | 11/1997 | Albright et al. | 514/211 |
| 5,693,635 | 12/1997 | Albright et al. | 514/215 |
| 5,696,112 | 12/1997 | Albright et al. | 514/215 |
| 5,700,796 | 12/1997 | Albright et al. | 514/220 |
| 5,719,278 | 2/1998 | Albright et al. | 540/578 |
| 5,733,905 | 3/1998 | Albright et al. | 514/220 |
| 5,736,538 | 4/1998 | Albright et al. | 514/215 |
| 5,736,540 | 4/1998 | Albright et al. | 514/220 |
| 5,739,128 | 4/1998 | Albright et al. | 514/220 |
| 5,747,487 | 5/1998 | Albright et al. | 514/215 |
| 5,753,648 | 5/1998 | Albright et al. | 514/220 |
| 5,760,031 | 6/1998 | Albright et al. | 514/215 |
| 5,780,471 | 7/1998 | Venkatesan et al. | 514/250 |

FOREIGN PATENT DOCUMENTS

| | | |
|---|---|---|
| 8-081460 | 3/1996 | (JP) . |
| 9534540 | 12/1995 | (WO) . |
| 9906351 * | 2/1999 | (WO) . |

OTHER PUBLICATIONS

Cervoni and Chan, Encylc. Of Chem. Tech., 4$^{th}$ ed., 8, 398–432 (1993).
Oliver et al., J. Physiol. (London), 18, 277–279 (1895).
du Vigneaud et al., J. Am. Chem. Soc., 76, 4751–4752 (1954).
Jackson, Pharm. Basis of Ther., 9$^{th}$ ed., 715–731 (1996).
Lethagen, Ann. Hematol., 69, 173–180 (1994).
Cash et al., Brit. J. Haematol, 27, 363–364 (1974).
David, Regulatory Peptides, 45, 311–317 (1993).
Burggraaf et al., Cli. Sci., 86, 497–503 (1994).
Manning et al., J. Med. Chem., 35, 382 (1992).
Manning et al., J. Med. Chem., 35, 3895 (1992).
Ruffolo et al., Drug News and Perspectives, 4(4), 217 (May 1991).
Albright et al., Curr. Pharm. Des., 3(6), 615 (1997).
Williams et al., J. Med. Chem., 35, 3905 (1992).
Huguenin et al., Helv. Chem. Acta, 49, 695 (1966) (translation).

* cited by examiner

Primary Examiner—Richard L. Raymond
Assistant Examiner—Sudhaker B. Patel
(74) Attorney, Agent, or Firm—Steven R. Eck

(57) ABSTRACT

The present invention provides compounds of the general formula:

(I)

as well as methods and pharmaceutical compositions utilizing these compounds for the inducement of temporary delay of urination or the treatment of disorders which may be remedied or alleviated by vasopressin agonist activity, including diabetes insipidus, nocturnal enuresis, nocturia, urinary incontinence, bleeding and coagulation disorders.

16 Claims, No Drawings

TRICYCLIC PYRIDINE N-OXIDES VASOPRESSIN AGONISTS

This application claims the benefit of U.S. Provisional Application No. 60/155,195, which was converted from U.S. patent application Ser. No. 09/244,680, filed Feb. 4, 1999, pursuant to a petition filed under 37 C.F.R. 1.53(c)(2)(i).

This invention concerns tricyclic pyridine N-oxides which act as vasopressin agonists, as well as methods of treatment and pharmaceutical compositions utilizing these compounds.

BACKGROUND OF THE INVENTION

Vasopressin (antidiuretic hormone, ADH) a nonapeptide hormone and neurotransmitter, is synthesized in the supraoptic nuclei of the hypothalamus of the brain and is transported through the supraoptico-hypophyseal tract to the posterior pituitary where it is stored. Upon sensing an increase in plasma osmolality by brain osmoreceptors or a decrease in blood volume or blood pressure (detected by the baroreceptors and volume receptors), vasopressin is released into the blood circulation and it activates $V_{1a}$ receptors on blood vessels causing vasoconstriction to raise blood pressure and vasopressin $V_2$ receptors of the nephron of the kidney causing reabsorption of water, and to a lesser degree electrolytes, to expand the blood volume (Cervoni and Chan, Diuretic Agents, in Kirk-Othmer, Encyclopedia of Chemical Technology, 4th ed., Wiley, Volume 8, 398–432, (1993)). The existence of vasopressin in the pituitary was known as early as 1895 (Oliver and Schaefer, J. Physiol. (London), 18, 277–279, (1895)). The determination of the structure and the total synthesis of vasopressin were accomplished by du Vigneaud and coworkers in 1954 (du Vigneaud, Gish and Katsoyannis, J. Am. Chem. Soc., 76, 4751–4752, (1954)).

The actions of vasopressin $V_{1a}$ receptors are mediated through the phosphatidylinositol pathway. Activation of vasopressin $V_{1a}$ receptors causes contraction of the smooth muscle of the blood vessels to raise blood pressure. The actions of the vasopressin $V_2$ receptors are mediated through activation of the adenylate cyclase system and elevation of intracellular levels of cAMP. The activation of vasopressin $V_2$ receptors by vasopressin or vasopressin-like (peptidic or non-peptidic) compounds increases water permeability of the collecting ducts of the nephron and permits the reabsorption of a large quantity of free water. The end result is the formation and excretion of a concentrated urine, with a decrease in urine volume and an increase in urinary osmolality.

Vasopressin plays a vital role in the conservation of water by concentrating the urine at the site of the collecting ducts of the kidney. The collecting ducts of the kidney are relatively impermeable to water without the presence of vasopressin at the receptors and therefore, the hypotonic fluid formed after filtering through the glomeruli, passing the proximal convoluted tubule, the loops of Henle, and the distal convoluted tubules, will be excreted as dilute urine. However, during dehydration, volume depletion or blood loss, vasopressin is released from the brain and activates the vasopressin $V_2$ receptors in the collecting ducts of the kidney rendering the ducts very permeable to water; hence water is reabsorbed and a concentrated urine is excreted. In patients and animals with central or neurogenic diabetes insipidus, the synthesis of vasopressin in the brain is defective and therefore, they produce no or very little vasopressin, but their vasopressin receptors in the kidneys are normal. Because they cannot concentrate the urine, they may produce as much as 10 times the urine volumes of their healthy counterparts and they are very sensitive to the action of vasopressin and vasopressin $V_2$ agonists. Vasopressin and desmopressin, which is a peptide analog of the natural vasopressin, are being used in patients with central diabetes insipidus. Vasopressin $V_2$ agonists are also useful for the treatment of nocturnal enuresis, nocturia, urinary incontinence and temporary delay of urination whenever desirable.

Vasopressin, through activation of its $V_{1a}$ receptors, exerts vasoconstricting effects so as to raise blood pressure. A vasopressin $V_{1a}$ receptor antagonist will counteract this effect. Vasopressin and vasopressin agonists release factor VIII and von Willebrand factor so they are useful for the treatment of bleeding disorders, such as hemophilia. Vasopressin and vasopressin-like agonists also release tissue-type plasminogen activator (t-PA) into the blood circulation so they are useful in dissolving blood clots such as in patients with myocardial infarction and other thromboembolic disorders (Jackson, "Vasopressin and other agents affecting the renal conservation of water", in Goodman and Gilman, The Pharmacological Basis of Therapeutics, 9th ed., Hadman, Limbird, Molinoff, Ruddon and Gilman Eds., McGraw-Hill, New York, pp. 715–731 (1996); Lethagen, Ann. Hematol. 69, 173–180 (1994); Cash et al., Brit. J. Haematol., 27, 363–364 (1974); David, Regulatory Peptides, 45, 311–317 (1993); Burggraaf et al., Cli. Sci., 86, 497–503 (1994)).

The following prior art references describe peptidic vasopressin antagonists: Manning et al., J. Med. Chem., 35, 382 (1992); Manning et al., J. Med. Chem., 35, 3895 (1992); Gavras and Lammek, U.S. Pat. No. 5,070,187 (1991); Manning and Sawyer, U.S. Pat. No. 5,055,448 (1991); Ali, U.S. Pat. No. 4,766,108 (1988); Ruffolo et al., Drug News and Perspectives 4(4), 217 (May 1991) and Albright and Chan, Curr. Pharm. Des., 3 (6), 615 (1997). Williams et al., have reported on potent hexapeptide oxytocin antagonists [J. Med. Chem., 35, 3905 (1992)] which also exhibit weak vasopressin antagonistic activity in binding to $V_1$ and $V_2$ receptors. Peptidic vasopressin antagonists suffer from a lack of oral activity and many of these peptides are non-selective antagonists since they also exhibit partial agonist activity.

Non-peptidic vasopressin antagonists have recently been disclosed. Albright et al. describe tricyclic azepines as vasopressin antagonists or vasopressin and oxytocin antagonists in U.S. Pat. No. 5,516,774 (1996), U.S. Pat. No. 5,532,235 (1996), U.S. Pat. No. 5,536,718 (1996), U.S. Pat. No. 5,610,156 (1997), U.S. Pat. No. 5,612,334 (1997), U.S. Pat. No. 5,624,923 (1997), U.S. Pat. No. 5,654,297 (1997), U.S. Pat. No. 5,686,445 (1997), U.S. Pat. No. 5,693,635 (1997), U.S. Pat. No. 5,696,112 (1997), U.S. Pat. No. 5,700,796 (1997), U.S. Pat. No. 5,719, 278 (1998), U.S. Pat. No. 5,733,905 (1998), U.S. Pat. No. 5,736,538 (1998), U.S. Pat. No. 5,736,540 (1998), U.S. Pat. No. 5,739,128 (1998Pat. No. 5,760,031 (1998), U.S. Pat. No. 5,780,471 (1998); tetrahydrobenzodiazepine derivatives as vasopressin antagonists are disclosed in J.P. 0801460-A (1996); Ogawa et al., disclose benzoheterocyclic derivatives as vasopressin and oxytocin antagonists, and as vasopressin agonists in WO 9534540-A; Albright et al., disclose tricyclic benzazepine derivatives as vasopressin antagonists in U.S. Pat. No. 5,512,563 (1996); and Venkatesan et al., disclose tricyclic benzazepine derivatives as vasopressin and oxytocin antagonists in U.S. Pat. No. 5,521,173 (1996).

As mentioned above, desmopressin (1-desamino-8-D-arginine vasopressin) (Huguenin and Boissonnas, Helv. Chim. Acta, 49, 695 (1966)) is a vasopressin agonist. The compound is a synthetic peptide with variable bioavailability. An intranasal route is poorly tolerated and an oral formulation for nocturnal enuresis requires a 10–20 fold greater dose than the intranasal administration.

The compounds of this invention as well as the compounds disclosed in AHP-97135, AHP-97266, AHP-97283, AHP-98369 and AHP-98370 are non-peptidic in nature and have a good oral bioavailability. They are vasopressin $V_2$ agonists and as such, they promote the reabsorption of water. The compounds of this invention also demonstrate no vasopressin V1a receptor agonist effects and thus, do not raise blood pressure. In contrast, the prior art compounds (except some in WO 9534540-A) are described as vasopressin antagonists at both the $V_{1a}$ and $V_2$ receptors.

SUMMARY OF THE INVENTION

This invention relates to novel compounds selected from those of Formula (I):

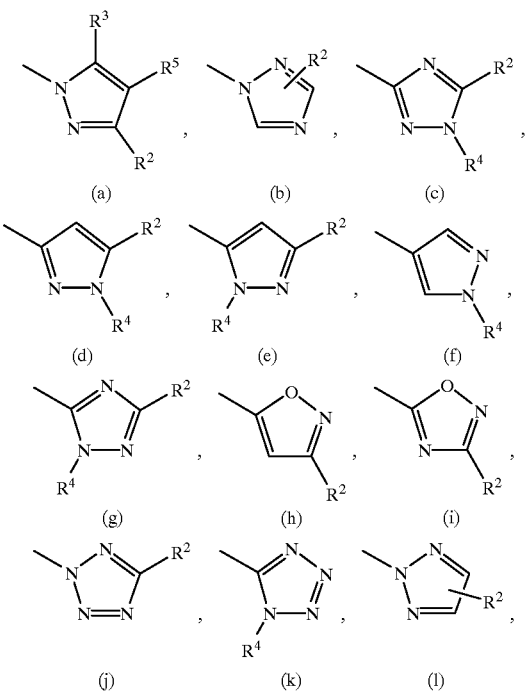

wherein:

$R^1$ is a group selected from:

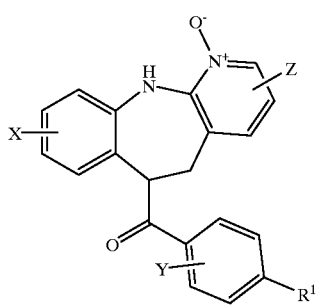

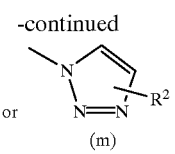

$R^2$, $R^3$ and $R^5$ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

$R^4$ is hydrogen, straight chain alkyl of 1 to 6 carbon atoms, branched chain alkyl of 3 to 7 carbon atoms, cycloalkyl of 3 to 7 carbon atoms, optionally substituted aralkyl of 7 to 15 carbon atoms;

X and Y are, independently, hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, halogen, straight or branched chain alkoxy of 1 to 6 carbon atoms, $CF_3$, or perfluoroalkyl of 2 to 6 carbons;

and Z is hydrogen, or straight chain alkyl group of 1 to 6 carbon atoms, or branched chain alkyl of 3 to 7 carbon atoms.

Among the more preferred compounds of this invention are those selected from Formula (I):

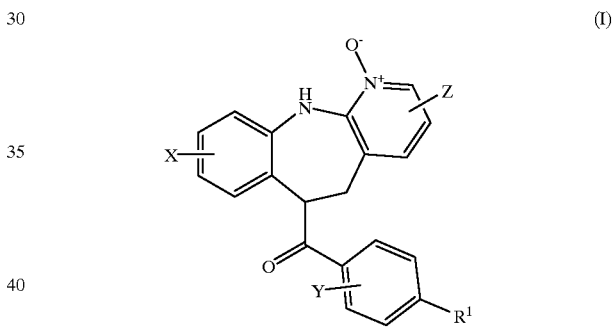

wherein:

$R^1$ is a group selected from

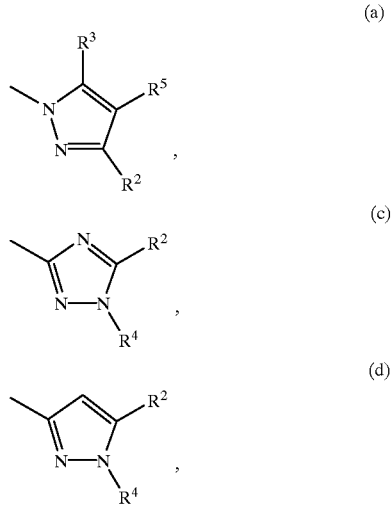

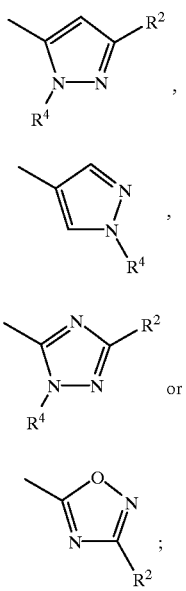

R², R³ and R⁵ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

R⁴ is hydrogen, straight chain alkyl of 1 to 6 carbon atoms, branched chain alkyl of 3 to 7 carbon atoms, cycloalkyl of 3 to 7 carbon atoms, or optionally substituted aralkyl of 7 to 15 carbon atoms;

X and Y are, independently, hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, halogen, straight chain or branched chain alkoxy of 1 to 6 carbons, CF₃, or perfluoroalkyl of 2 to 6 carbons;

and Z is hydrogen, or straight chain alkyl group of 1 to 6 carbon atoms, or branched chain alkyl of 3 to 7 carbon atoms.

For the compounds defined above and referred to herein, unless otherwise noted, aralkyl refers to groups such as benzyl or naphthylmethyl containing an alkyl residue, preferably a lower alkyl residue of from 1 to 6 carbon atoms, most preferably from 1 to 3 carbon atoms, terminally substituted by an aryl, wherein the aryl group is as defined hereinbefore.

For the compounds defined above and referred to herein, unless otherwise noted, the term halogen is meant to include chlorine, bromine, fluorine and iodine.

The preferred compounds of this invention are:
[2-Chloro-4-(3-methyl-1H-pyrazol-1-yl)-phenyl]-(6,11-dihydro-5H-pyrido[2,3-b][1,5]benzodiazepin-6-yl)-methanone-1-oxide;
[2-Chloro-4-(5-methyl-1H-pyrazol-1-yl)-phenyl]-(6,11-dihydro-5H-pyrido[2,3-b][1,5]benzodiazepin-6-yl)-methanone-1-oxide;
[2-Bromo-4-(3-methyl-1H-pyrazol-1-yl)-phenyl]-(6,11-dihydro-5H-pyrido[2,3-b][1,5]benzodiazepin-6-yl)-methanone-1-oxide;
[4-(3-Methyl-1H-pyrazol-1-yl)-2-(trifluoromethyl)-phenyl]-(6,11-dihydro-5H-pyrido[2,3-b][1,5]benzodiazepin-6-yl)-methanone-1-oxide;
[4-(5-Methyl-1H-pyrazol-1-yl)-2-(trifluoromethyl)-phenyl]-(6,11-dihydro-5H-pyrido[2,3-b][1,5]benzodiazepin-6-yl)-methanone-1-oxide;
{2-(Trifluoromethyl)-4-[3-(trifluoromethyl)-1H-pyrazol-1-yl]-phenyl}-(6,11-dihydro-5H-pyrido[2,3-b][1,5]benzodiazepin-6-yl)-methanone-1-oxide;
[2-Fluoro-4-(3-methyl-1H-pyrazol-1-yl)-phenyl]-(6,11-dihydro-5H-pyrido[2,3-b][1,5]benzodiazepin-6-yl)-methanone-1-oxide;
[4-Fluoro-2-(3-methyl-1H-pyrazol-1-yl)-phenyl]-(6,11-dihydro-5H-pyrido[2,3-b][1,5]benzodiazepin-6-yl)-methanone-1-oxide;
[2-Methyl-5-(3-methyl-1H-pyrazol-1-yl)-phenyl]-(6,11-dihydro-5H-pyrido[2,3-b][1,5]benzodiazepin-6-yl)-methanone-1-oxide;
[4-(3-tert-Butyl-1H-pyrazol-1-yl)-2-(trifluoromethyl)-phenyl]-(6,11-dihydro-5H-pyrido[2,3-b][1,5]benzodiazepin-6-yl)-methanone-1-oxide;
[2-Chloro-4-(1-methyl-1H-pyrazol-3-yl)-phenyl]-(6,11-dihydro-5H-pyrido[2,3-b][1,5]benzodiazepin-6-yl)-methanone-1-oxide; and
[2-Chloro-4-(5-methyl-1H-[1,2,4]triazol-3-yl)-phenyl]-(6,11-dihydro-5H-pyrido[2,3-b][1,5]benzodiazepin-6-yl)-methanone1-oxide.

It is understood by those practicing the art that some of the compounds of this invention depending on the definition of R², R³, R⁴, R⁵, X, Y, and Z may contain one or more asymmetric centers and may thus give rise to optical isomers and diastereomers. The present invention includes such optical isomers and diastereomers; as well as the racemic and resolved, enantiomerically pure R and S stereoisomers; as well as other mixtures of the R and S stereoisomers and pharmaceutically acceptable salts thereof, which possess the indicated activity. Optical isomers may be obtained in pure form by standard procedures known to those skilled in the art. It is also understood that this invention encompasses all possible regioisomers, and mixtures thereof which possess the indicated activity. Such regioisomers may be obtained in pure form by standard separation procedures known to those skilled in the art.

Also according to the present invention there is provided a method of treating disorders which are remedied or alleviated by vasopressin agonist activity including, but not limited to, diabetes insipidus, nocturnal enuresis, nocturia, urinary incontinence, bleeding and coagulation disorders, and temporary delay of urination whenever desirable in humans or other mammals, which comprises administering to a human or other mammal an effective amount of a compound or a pharmaceutical composition of the invention.

The present invention accordingly provides a pharmaceutical composition which comprises a compound of this invention in combination or association with a pharmaceutically acceptable carrier or excipient. In particular, the present invention provides a pharmaceutical composition which comprises an effective amount of a compound of this invention and a pharmaceutically acceptable carrier or excipient.

The compositions are preferably adapted for oral administration. However, they may be adapted for other modes of administration, for example, parenteral administration for patients suffering from coagulation disorders.

In order to obtain consistency of administration, it is preferred that a composition of the invention is in the form of a unit dose. Suitable unit dose forms include tablets, capsules and powders in sachets or vials. Such unit dose forms may contain from 0.1 to 1000 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day. The compositions of the invention may be formulated with conventional excipients, such as a filler, a disintegrating agent, a binder, a lubricant, a flavoring agent and the like. They are formulated in conventional manner, for example, in a manner similar to that used for known antihypertensive agents, diuretics and β-blocking agents.

Also according to the present invention there are provided processes for producing the compounds of the present invention.

PROCESS OF THE INVENTION

The compounds of the present invention may be prepared according to one of the general processes outlined below. The compounds of general formula (I) can be conveniently prepared as shown in Scheme I.

dride of general formula (2) with a pyridobenzodiazepine of formula (1) in a solvent such as dichloromethane and in the presence of an organic base such as 4-dimethylaminopyridine at temperatures ranging from 0° C. to the reflux temperature of the solvent, yields the intermediate acylated derivative (3) of Scheme I.

A compound of formula (3) is then treated with the sodium (potassium or lithium) salt of an appropriately substituted heterocycle of formula (4, wherein $R^1$ is selected from the (a), (b), (j), (l), (m) group of heterocycles defined above) in an aprotic organic solvent such as dimethylformamide (or tetrahydrofuran) at temperatures ranging from ambient to the reflux temperature of the solvent, to yield a compound of general formula (5). Treatment of the latter with an oxidizing agent such as a peracid acid, methyltrioxorhenium-$H_2O_2$ or other pyridine oxidizing agents known in the literature (see Coperet et al., *J. Org. Chem.*, 63, 1740–1741 (1998) and references therein) at temperatures ranging from −40° C. to ambient temperature,

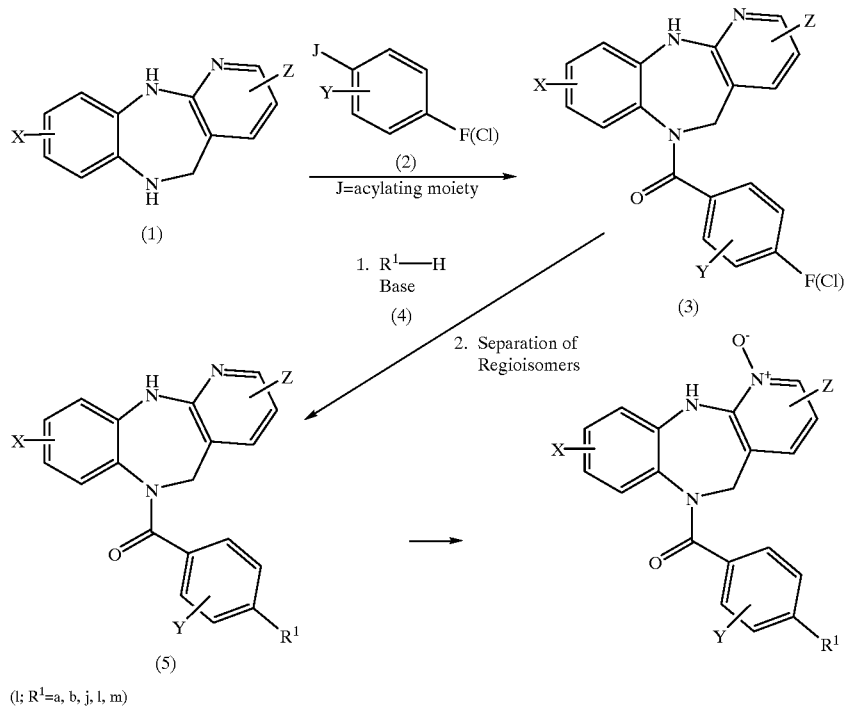

Scheme I

Thus, a pyridobenzodiazepine of formula (1) is treated with an appropriately substituted haloaroyl halide, preferably a fluoroaroyl chloride of formula (2, J=COCl), in the presence of an inorganic base such as potassium carbonate in a polar, aprotic solvent such as dimethylformamide; or an organic base such as 4-dimethylaminopyridine in an aprotic solvent such as dichloromethane or tetrahydrofuran at temperatures ranging from −40° C. to 50° C. to yield the intermediate acylated derivative (3).

Alternatively, the acylating species can be a mixed anhydride of the corresponding carboxylic acid, such as that prepared treating said acid with 2,4,6-trichlorobenzoyl chloride in an aprotic organic solvent such as dichloromethane according to the procedure of Inanaga et al., *Bull. Chem. Soc. Jpn.*, 52, 1989 (1979). Treatment of said mixed anhyprovides a compound of general formula (I) wherein X, Y, Z, $R^2$, $R^3$, and $R^5$ are as defined above, and $R^1$ is an heterocyclic moiety selected from the (a), (b), (j), (l), (m) group of heterocycles defined above and illustrated below.

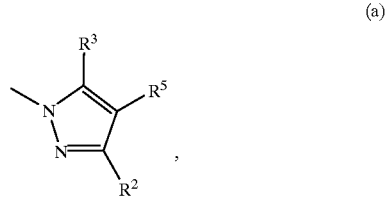

(a)

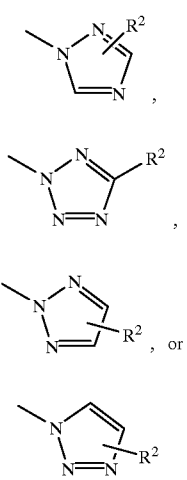

(b), (j), (l), (m)

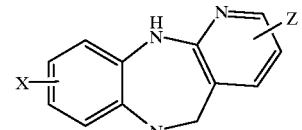

(10)

J = Acylating Agent

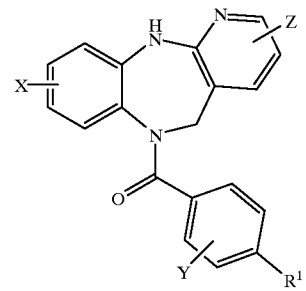

(1)

(5; R¹ = a, b, j, l, or m)

The condensation of the intermediate of formula (3) with the intermediate salt of formula (4) leads to a variable ratio of regioisomers of formula (5) which are separated by means of chromatography and/or crystallization.

The preferred substituted fluoroaroyl chlorides of formula (2) of Scheme I are either available commercially, or are known in the art, or can be readily prepared by procedures analogous to those in the literature for the known compounds.

The sodium (potassium or lithium) salts of the heterocycle of formula (4, wherein R¹ is selected from the (a), (b), (j), (l), (m) group of heterocycles defined above) of Scheme I are prepared by treatment of said heterocycle with a strong base such as sodium, potassium or lithium hydride or a metal alkoxide at temperatures ranging from −40° C. to ambient in an aprotic organic solvent such as dimethylformamide or tetrahydrofuran.

Alternatively, the compounds of formula (5) described in Scheme I can be prepared according to the process outlined in Scheme II.

Scheme II

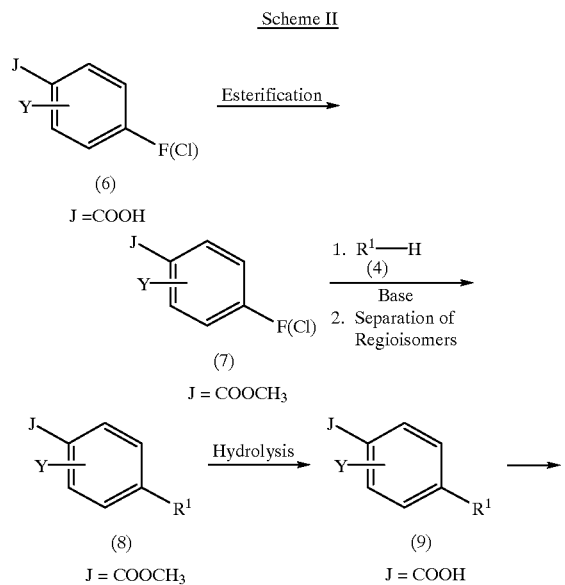

Thus, an appropriately substituted fluoroaryl carboxylic acid of formula (6) is esterified using methods known in the art, such as treatment with oxalyl chloride or thionyl chloride in an alcohol solvent such as methanol, in the presence of a catalytic amount of dimethylformamide; or by condensation with an alcohol such as methanol, in the presence of an acid catalyst such as para-toluenesulfonic acid at temperatures ranging from ambient to reflux temperature of the solvent.

The resulting ester of formula (7) is reacted with the sodium (potassium or lithium) salt of an appropriately substituted heterocycle of formula (4, wherein R¹ is selected from the (a), (b), (j), (l), (m) groups of heterocycles defined above) in a polar aprotic organic solvent such as dimethylformamide at temperatures ranging from ambient to reflux temperature of the solvent, to yield an intermediate ester of general formula (8). The condensation of (7) with (4) leads to a variable ratio of regioisomers of general formula (8) which are separated by means of chromatography and/or crystallization.

Subsequent hydrolysis of the intermediate ester of formula (8) with an aqueous base such as sodium hydroxide in methanol (or lithium hydroxide in tetrahydrofuran) affords the carboxylic acid of general formula (9).

The intermediate carboxylic acid (9) is then converted into an acylating agent, preferably an acid chloride or a mixed anhydride of general formula (10) using any of the procedures described hereinbefore.

Subsequent condensation of the pyridobenzodiazepine of formula (1) with the intermediate acylating agent of formula (10) according to any of the procedures described hereinbefore, yields the desired compounds of formula (5) of Scheme I, wherein R¹ is selected from the (a), (b), (j), (l), (m) groups of heterocycles defined above.

The appropriately substituted fluoroaryl carboxylic acids of formula (6) of Scheme II are either available commercially, or are known in the art, or can be readily prepared by procedures analogous to those in the literature for known compounds.

Alternatively, the substituted carboxylic acids of formula (9 wherein Y is not $CF_3$) of Scheme II can be prepared according to the process outlined in Scheme III.

Scheme III

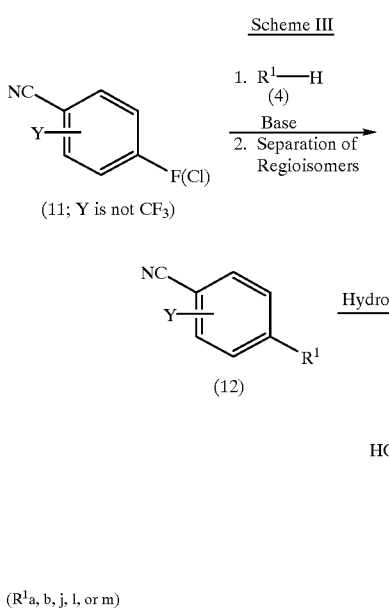

Thus, a fluoroaryl nitrile of formula (11) is reacted with the sodium (potassium or lithium) salt of an appropriately substituted heterocycle of formula (4), wherein $R^1$ is selected from the (a), (b), (j), (l), (m) groups of heterocycles defined above) in a polar aprotic organic solvent such as dimethylformamide at temperatures ranging from ambient to the reflux temperature of the solvent, to yield an intermediate of general formula (12). Condensation of (11) with the intermediate (4) leads to a variable ratio of regioisomers of general formula (12) which are separated by means of chromatography and/or crystallization. Hydrolysis of the intermediate nitrile of formula (12, wherein Y is not $CF_3$) is preferentially carried out with an inorganic acid such as dilute sulfuric acid, at temperatures ranging from ambient to 60° C.

Alternatively, hydrolysis of the nitrile (12) can be carried out by heating in the presence of a strong alkaline base such as sodium hydroxide in an alcohol solvent such as ethanol, with or without a phase transfer catalyst such as benzyldimethyltetradecyl ammonium chloride.

The resulting carboxylic acid of formula (9) is then converted into the desired compounds of formula (5) of Scheme I (wherein $R^1$ is selected from the (a), (b), (j), (l), (m) groups of heterocycles defined above) by procedures analogous to those described hereinbefore.

The appropriately substituted fluoroaryl nitrites of formula (11) of Scheme III are either available commercially, or are known in the art, or can be readily prepared by procedures analogous to those in the literature for known compounds.

Alternatively, the intermediate substituted carboxylic acids of formula (9) of Scheme II can be prepared according to the process described in Scheme IV by sequential treatment of a nitrite of formula (12, wherein $R^1$ is an heterocyclic moiety selected from the (a), (b), (j), (l), (m) groups of heterocycles defined above) with basic hydrogen peroxide in dimethylsulfoxide essentially according to the procedure of Katritzky et al., *Synthesis*, 949 (1989); followed by hydrolysis of the resulting amides of formula (13) preferably by treatment with dilute sulfuric acid and sodium nitrite according to the procedure of Hales et al, *Tetrahedron*, 51, 7403 (1995).

Scheme IV

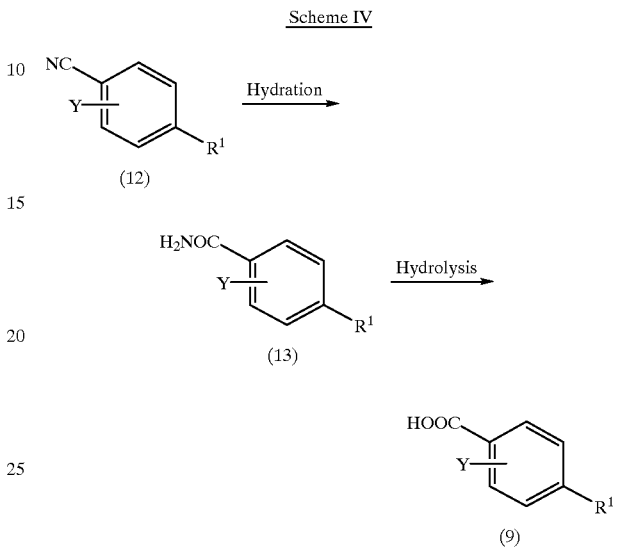

A preferred process for the preparation of the intermediate substituted carboxylic acids of formula (9) of Scheme II wherein $R^1$ is an heterocyclic moiety selected from the (a) group of $R^1$ heterocycles defined above, is outlined in Scheme V.

Scheme V

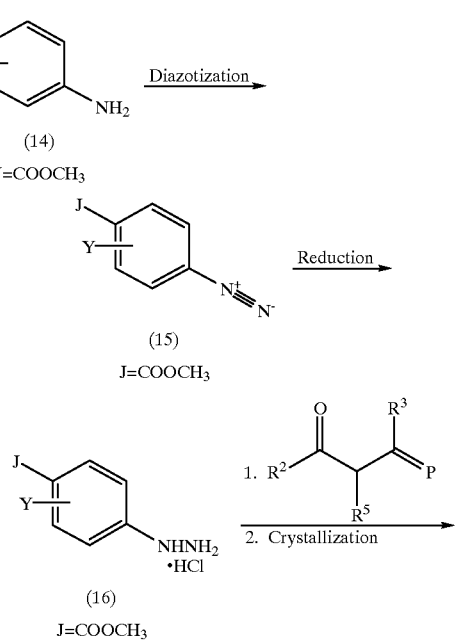

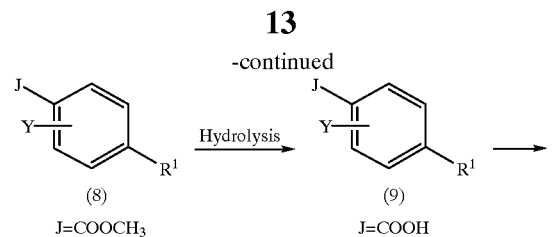

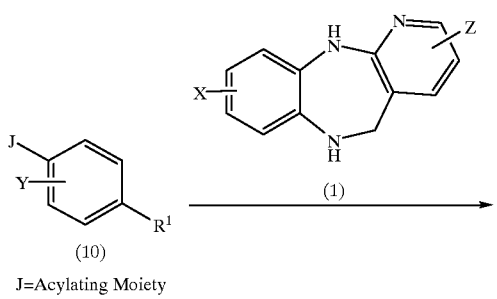

Thus, diazotization of an appropriately substituted aniline of general formula (14) followed by reduction of the resulting diazonium salt of formula (15) with tin (II) chloride in concentrated hydrochloric acid according to the procedure of Street et al., *J. Med. Chem.*, 36, 1529 (1993) provides the intermediate hydrazine hydrochloride salt of formula (16). Subsequent condensation of (16) with an aldehyde derivative of formula 35 (wherein $R^2$ and $R^5$ are as defined above, $R^3$ is hydrogen, and P is a dialkylacetal) such as acetylacetaldehyde dimethyl acetal, or a ketone (or a ketone derivative) of formula 35, (wherein $R^2$ and $R^5$ are as defined above, $R^3$ is not hydrogen, and P is O or a ketal) in a solvent such as aqueous methanol at temperatures ranging from ambient to 100° C. provides after crystallization, the desired intermediate ester of formula 8 (wherein $R^1$ is selected from the a group of heterocycles defined above), which is then converted to the compound of formula 5 (wherein $R^1$ is selected from the (a) group of heterocycles defined above and illustrated below) as outlined in Scheme II above.

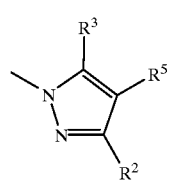

The compounds of general formula (5) of Scheme I wherein $R^2$ is hydrogen, and $R^1$ is an heterocyclic moiety selected from the (e) group of heterocycles defined above, may be prepared according to the general process outlined in Scheme VI.

Scheme VI

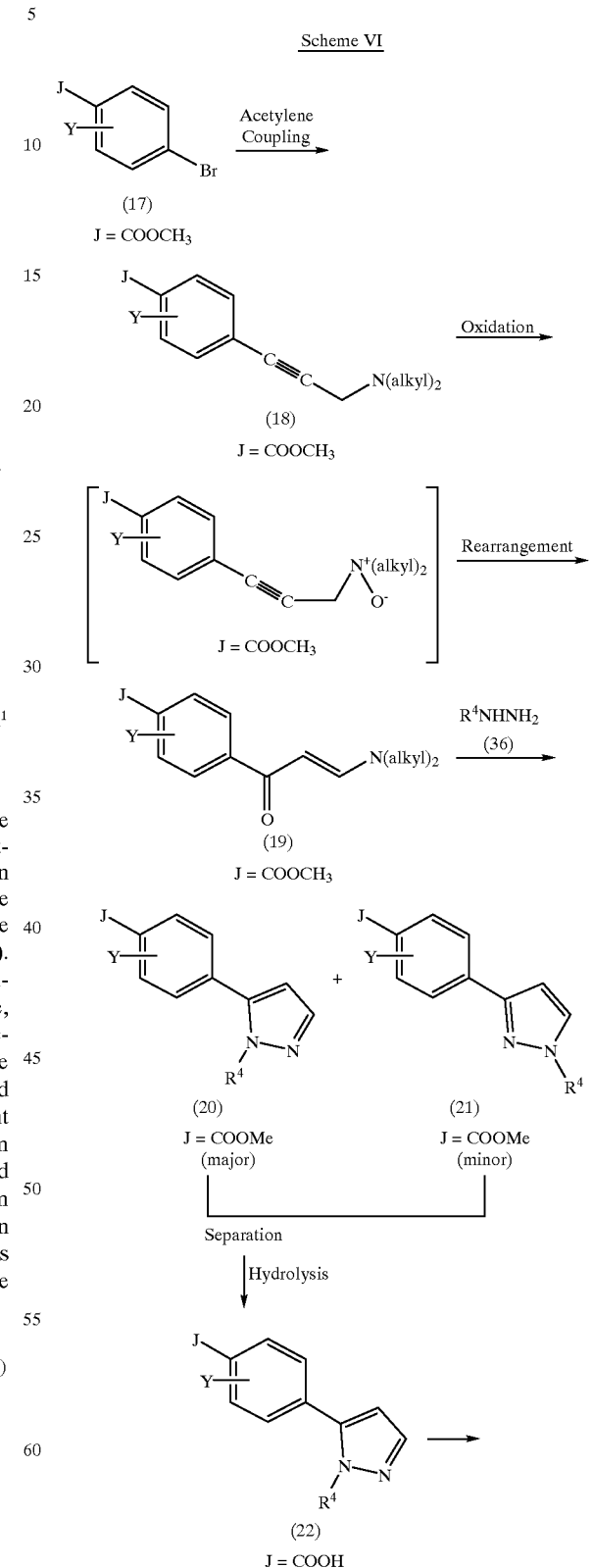

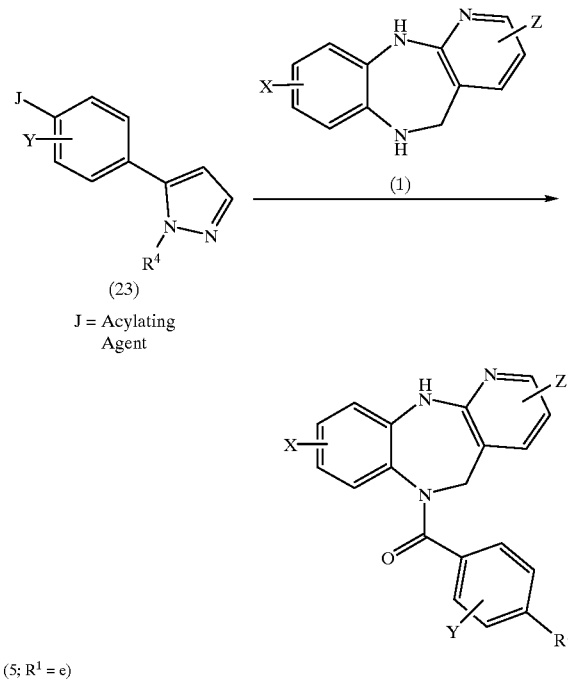

Thus, an appropriately substituted haloaryl carboxylic acid ester, preferably a bromo (or iodo)phenyl methyl ester of formula (17) is coupled with a dialkylamino propyne, in the presence of a catalyst such as bis(triphenylphosphine) palladium (II) chloride and copper (I) iodide in an organic base such as triethylamine as the solvent, and at temperatures ranging from ambient to 80° C. essentially according to the procedures of Alami et al., *Tetrahedron Lett.,* 34, 6403 (1993), and of Sanogashira et al., *Tetrahedron Lett.,* 16, 4467 (1975), to provide the substituted acetylene intermediate of general formula (18).

The intermediate (18) is subsequently converted into its N-oxide by treatment with an oxidizing agent using any of a number of standard oxidative procedures (see Albini, *Synthesis,* 263, (1993)) or with a dioxirane reagent (see Murray, *Chem. Rev.,* 1187 (1989)) in an aprotic organic solvent such as dichloromethane at temperatures below ambient.

The intermediate N-oxide in these steps is not isolated but is rearranged in situ to an enone of general formula (19) in the presence of a hydroxylic solvent, for instance with heating in a hydroxylic solvent such as methanol. The conversion of the amine N-oxide into an enaminone may be accomplished by a number of treatments with one or more hydroxylic solvents. The amine N-oxide may be introduced into a suitable hydroxylic solvent, preferably with stirring, at or between about room or ambient temperature and about the reflux temperature of the solvent. In other instances the introduction of the amine N-oxide to a hydroxylic solvent, preferably with stirring, may be accomplished in the presence of an acceptable catalyst, such as a palladium(II) catalyst or a copper (I) catalyst, at or between room temperature and the reflux temperature of the solvent.

In instances where a biphasic solvent system is desirable, the amine N-oxide may be converted into the enaminone in a biphasic mixture of water and a water immiscible solvent, such as dichloromethane, in the presence or absence of a suitable catalyst, such as a palladium(II) catalyst or a copper (I) catalyst, and a phase transfer catalyst, such as a quaternary ammonium salt, at or between ambient temperature and the reflux temperature of the organic solvent, preferably with stirring.

The hydroxylic solvents useful with these methods may be defined as any solvent or combination of solvents composed of or containing water, any $C_1$–$C_8$ straight chain or branched chain alkyl alcohol, ethylene glycol, polyethylene glycol, 1,2-propylene diol, polypropylene glycol, glycerol, 2-methoxyethanol, 2-ethoxyethanol, 2,2,2-trifluoroethanol, benzyl alcohol, phenol, or any equivalent solvent known to those skilled in the art that contains one or more of the free hydroxyl (—OH) substituent(s).

Solvent systems containing one or more cosolvents, along with one or more solvents may be used for the processes of this invention. The cosolvents referred to herein may be defined as a diluent of the main solvent(s) and can be selected from: hydrocarbons such as pentane, hexane or heptane; aromatic hydrocarbon such as benzene, toluene or xylene; ethers such as diethyl ether, tetrahydrofurn, dioxane or dimethoxy ethane; chlorinated hydrocarbons such as dichloromethane, chloroform, dichloroethane, or tetrachloroethane; or other common solvents such as ethyl acetate, N,N-dimethylformamide, N,N-dimethylacetamide, acetonitrile, dimethylsulfoxide, acetone, or the like.

Although the precise mechanism by which a propargylic amine N-oxide is converted into an enaminone product has not been rigorously determined, it likely resembles two known processes; the thermal [2,3]-sigmatropic rearrangement of propargylic amine N-oxides (Craig et al., *Tetrahedron Lett.,* 4025, (1979); Hallstrom, et al., *Tetrahedron Lett.,* 667, (1980); Khuthier, A-H, et al., *J. Chem. Soc. Chem. Commun.,* 9, (1979)) and the conversion of certain isoxazoles into enaminones (Liguori, et al., *Tetrahedron,* 44, 1255 (1988)).

Treatment of (19) with a substituted hydrazine (36) in acetic acid at temperatures ranging from ambient to reflux leads to a mixture of regioisomeric compounds of general formulas (20) and (21) in a variable ratio. The major isomer of formula (20, wherein $R^2$ is H) is separated by means of chromatography and/or crystallization and is subsequently hydrolyzed to the desired carboxylic acid of formula (22).

The intermediate (22) is then converted into an acylating species, preferably an acid chloride (bromide or iodide) or a mixed anhydride of formula (23) by procedures analogous to those described hereinbefore. The acylating agent (23) is then used to acylate a pyridobenzodiazepine of formula (1) by any of the procedures described hereinbefore to yield the desired compound of formula (5), wherein X, Y, Z, and $R^4$ are as defined above, $R^2$ is hydrogen, and $R^1$ is an heterocyclic moiety selected from the (e) group of heterocycles defined above and illustrated below

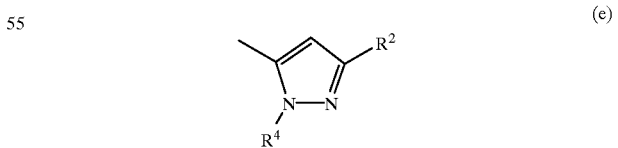

Likewise, treatment of (19) with an unsubstituted hydrazine (36, wherein $R^4$ is H) in acetic acid at temperatures ranging from ambient to the reflux temperature of the solvent yields the intermediate pyrazole ester of formula (24, $R^2$ and $R^4$ are H) as shown in Scheme VII. In this case the pyrazole nitrogen of (24) can be alkylated or acylated to provide intermediates which can be converted to compounds of formula (5) wherein X, Y, Z, and $R^4$ are as defined above, $R^2$ is hydrogen, and $R^1$ is an heterocyclic moiety selected from the (d) group of heterocycles defined above.

Scheme VII

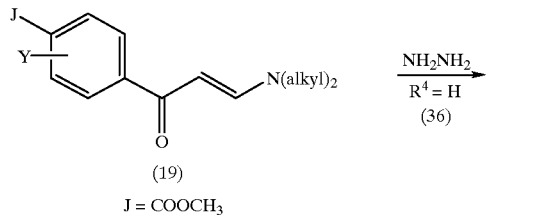
(19)
J = COOCH$_3$

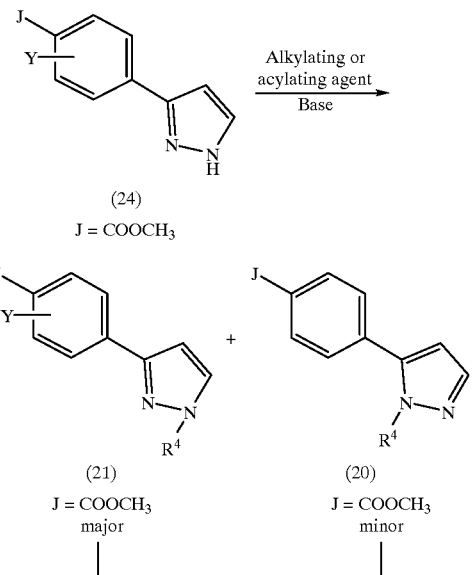

(25)
J = COOH

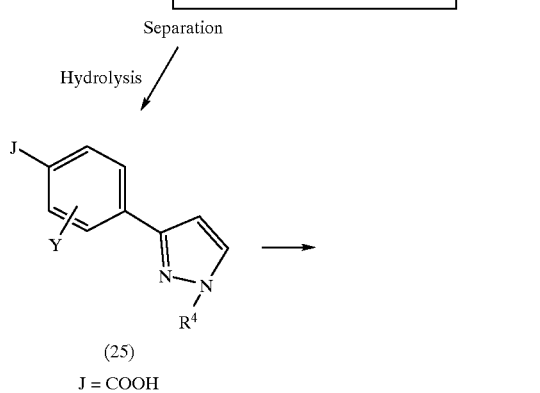
(26)
J = acylating moiety

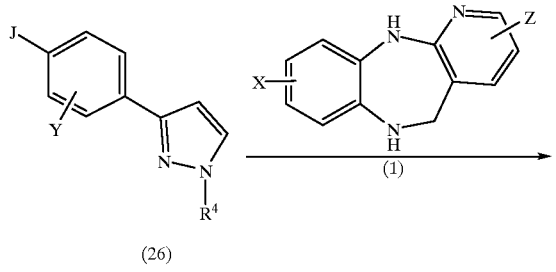
(5, $R^1$ = d)

Thus, the intermediate ester of formula (24, wherein $R^2$ is H) is alkylated by treatment with a base such as sodium or potassium hydride and an alkylating agent such as an alkyl halide, preferably an alkyl chloride (bromide or iodide) in an aprotic solvent such as dimethylformamide or tetrahydrofuran at temperatures ranging from 0° C. to 80° C. to yield a mixture of regioisomers of formulas (20) and (21) in a variable ratio. The major regioisomer of formula (21) is separated by chromatography and/or crystallization and is subsequently hydrolyzed to the desired carboxylic acid of formula (25), which is then converted to an acylating agent, preferably an acid chloride or a mixed anhydride by procedures analogous to those described hereinbefore. The acylating species of formula (26) is then used to acylate a pyridobenzodiazepine of formula (1) to yield the desired compound of formula (5), wherein X, Y, Z, and $R^4$ are as defined above, $R^2$ is hydrogen, and $R^1$ is an heterocyclic moiety selected from the (d) group of heterocycles defined above and illustrated below.

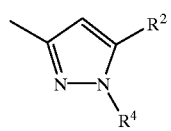
(d)

Compounds of general formula (5) wherein $R^1$ is an heterocyclic moiety selected from the (f) group of heterocycles defined above, can be prepared as outlined in Scheme VIII.

Scheme VIII

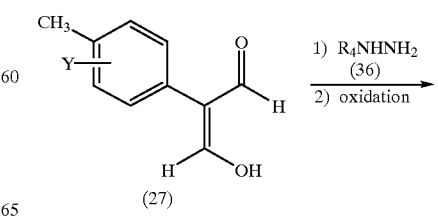
(27)

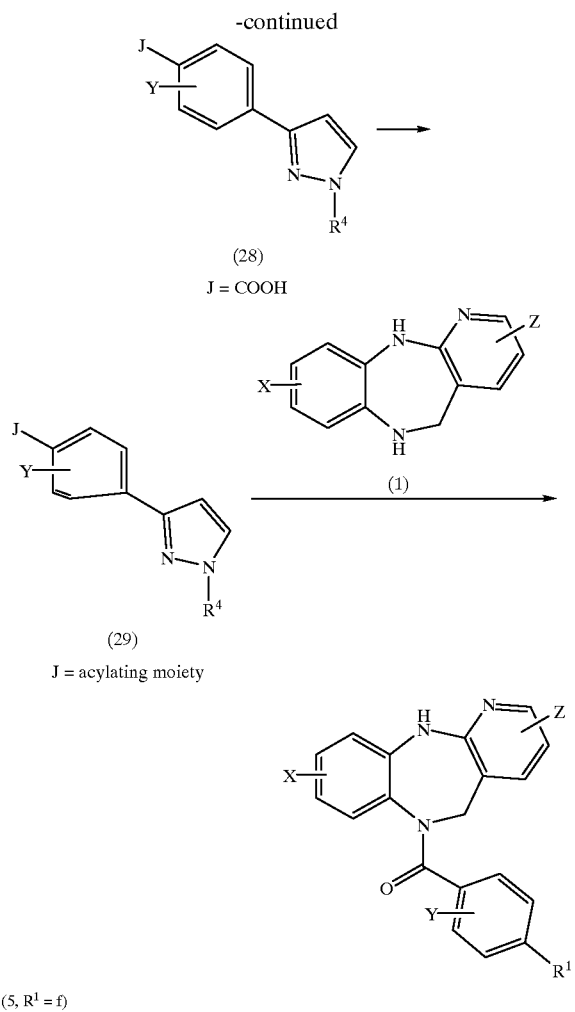

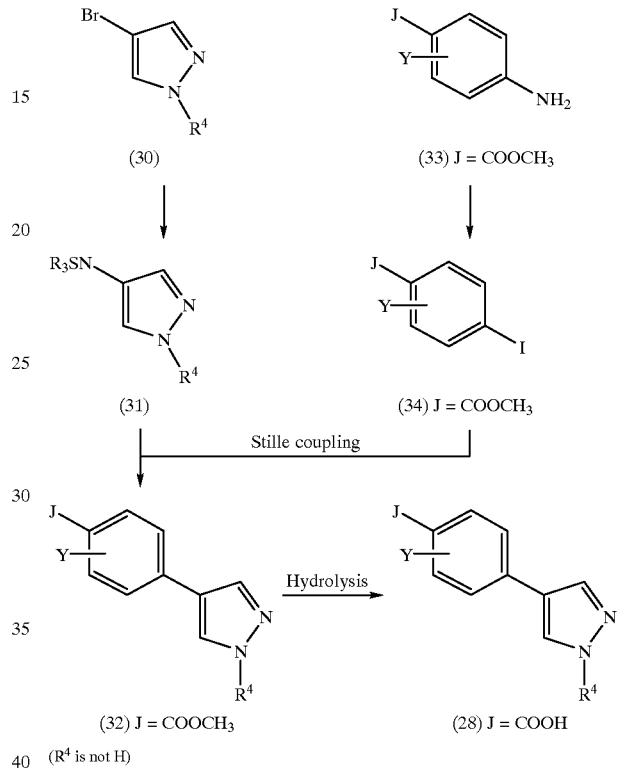

($R^4$ is not H)

An appropriately substituted malondialdehyde of formula (27) is treated first with a hydrazine in acetic acid at temperatures ranging from ambient to the reflux temperature of the solvent and the intermediate pyrazole is oxidized preferably with potassium permanganate in a basic aqueous solution at temperatures ranging from ambient to the reflux temperature of the solvent to yield a carboxylic acid intermediate of formula (28). The acid (28) is converted into an acylating agent, preferably an acid chloride (bromide or iodide) or a mixed anhydride by procedures analogous to those described hereinbefore. The acylating agent of formula (29) is finally reacted with a pyridobenzodiazepine of formula (1) to yield compounds of general formula (5) wherein X, Y, Z, and $R^4$ are as defined above, and $R^1$ is an heterocyclic moiety selected from the (f) group of heterocycles defined above and illustrated below.

(f)

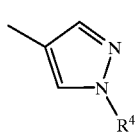

The preferred malondialdehydes of formula (27) and the hydrazines (36) of Scheme VIII are either available commercially, or are known in the art, or can be readily prepared by procedures analogous to those in the literature for known compounds, such as those of Knorr et al., *J. Org. Chem.*, 49, 1288 (1984) and Coppola et al., *J. Het. Chem.*, 51 (1974).

An alternative preparation of the intermediate carboxylic acids of formula (28) of Scheme VIII wherein Y is as defined above and $R^4$ is other than hydrogen, is outlined in Scheme IX.

An organotin reagent of formula (31) is reacted in a Stille coupling reaction with an appropriately substituted aryl halide, preferably a bromide (or iodide) of formula (34) in the presence of a catalyst such as tetrakis (triphenylphosphine) palladium (O) and copper (I) iodide in an organic aprotic solvent such as dimethylformamide at temperatures ranging from ambient to 150° C., essentially according to procedures analogous to those of Farina et al., *J. Org. Chem.*, 59, 5905 (1994). Basic hydrolysis of the resulting ester of formula (32) with sodium hydroxide in aqueous alcohol or lithium hydroxide in aqueous tetrahydrofuran at temperatures ranging from ambient to the reflux temperature of the solvent yields the desired carboxylic acids of formula (28) of Scheme VIII.

In turn, the organotin reagents of formula (31) of Scheme IX wherein R is preferably an alkyl group, are conveniently prepared by metallation of a 4-bromo-N-alkylpyrazole of formula (30) with a trialkyltin halide, preferably a tributyltin chloride (or bromide) in the presence of a metallating agent such as n-butyl lithium in an aprotic organic solvent such as diethyl ether at temperatures ranging from −40° C. to ambient according to procedures analogous to those found in Martina et al., *Synthesis*, 8, 613 (1991).

The preferred N-alkyl substituted pyrazoles of formula (30) of Scheme IX are conveniently prepared from a 4-bromopyrazole by alkylation with an alkyl halide, preferably an alkyl chloride (bromide or iodide) in the presence of a base such as sodium (or potassium) hydride in an aprotic organic solvent such as dimethylformamide or tetrahydrofuran at temperatures ranging from 0° C. to 80° C. Alternatively, alkylation of the 4-bromopyrazole can be carried out with an alkylating agent mentioned above, and a strong alkaline base such as sodium hydroxide in the presence of a phase transfer catalyst, such as benzyldimethyltetradecyl ammonium chloride or benzyl trimethyl ammonium chloride (see Jones, *Aldrichimica Acta*, 9, 35 (1976)).

The preferred aryl iodides of formula (34) of Scheme IX are conveniently prepared by diazotization of the corresponding substituted anilines of formula (33) followed by reaction of the corresponding diazonium salt with iodine and potassium iodide in aqueous acidic medium essentially according to the procedures of Street et al., *J. Med. Chem.*, 36, 1529 (1993) and of Coffen et al., *J. Org. Chem.*, 49, 296 (1984).

The compounds of general formula (5) may be prepared also according to one of the general processes outlined below.

As shown in Scheme X, a pyridobenzodiazepine of formula (1) is treated with an appropriately substituted acetylaroyl halide preferably an acetylaroyl chloride of formula 37(J=COCl) according to any of the procedures described hereinbefore, to yield the acylated derivative of formula (38). Treatment of (38) with a dialkylamide dialkylacetal such as a dimethylamide dimethyl acetal of formula 39 (where alkyl is $CH_3$), in an aprotic organic solvent such as dichloromethane at temperatures ranging from 0° C. to the reflux temperature of the solvent according to the procedure of Lin et al., *J. Het. Chem.*, 345 (1977) yields the enone of formula (40). Treatment of (40) with hydroxylamine or a substituted hydrazine of formula (36) in acetic acid at temperatures ranging from ambient to the reflux temperature of the solvent provides the target compounds of formula (5) wherein X, Y, Z, $R^2$ and $R^4$ are as defined above, and $R^1$ is an heterocyclic moiety selected from the (d), (e), or (h) group of heterocycles defined above and illustrated below.

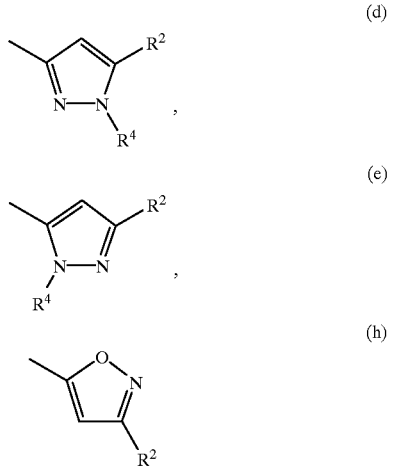

The preferred substituted acetylaroyl chlorides of formula (37) of Scheme X are conveniently prepared by treating the corresponding carboxylic acids with thionyl chloride at temperatures ranging from ambient to the reflux temperature of the solvent, or with oxalyl chloride in an aprotic solvent such as dichloromethane or tetrahydrofuran in the presence of a catalytic amount of dimethylformamide at temperatures ranging from 0° C. to 40° C.

The preferred dialkylamide dialkylacetals of formula (39) of Scheme X are either available commercially, or are known in the literature, or can be conveniently prepared according to procedures analogous to those in the literature for the known compounds (see Kantlehner, *Chem. Ber.*, 105, 1340 (1972)).

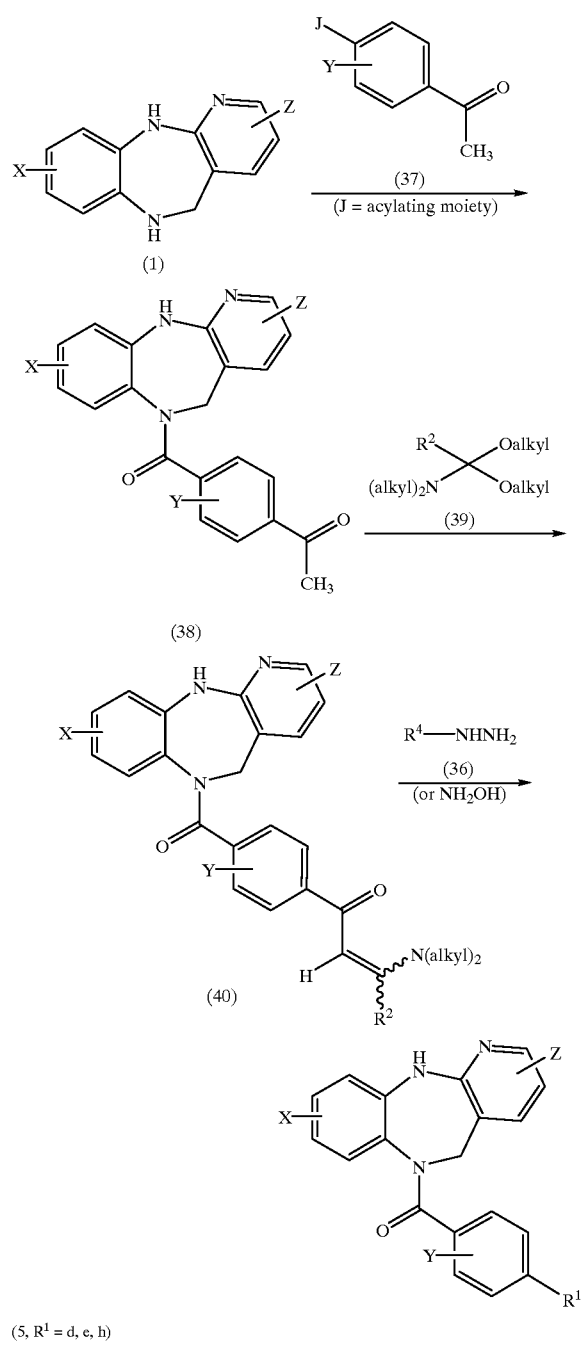

Scheme X

An alternate process for the preparation of intermediates of formula (38) of Scheme X is illustrated in the following Scheme XI.

Scheme XI

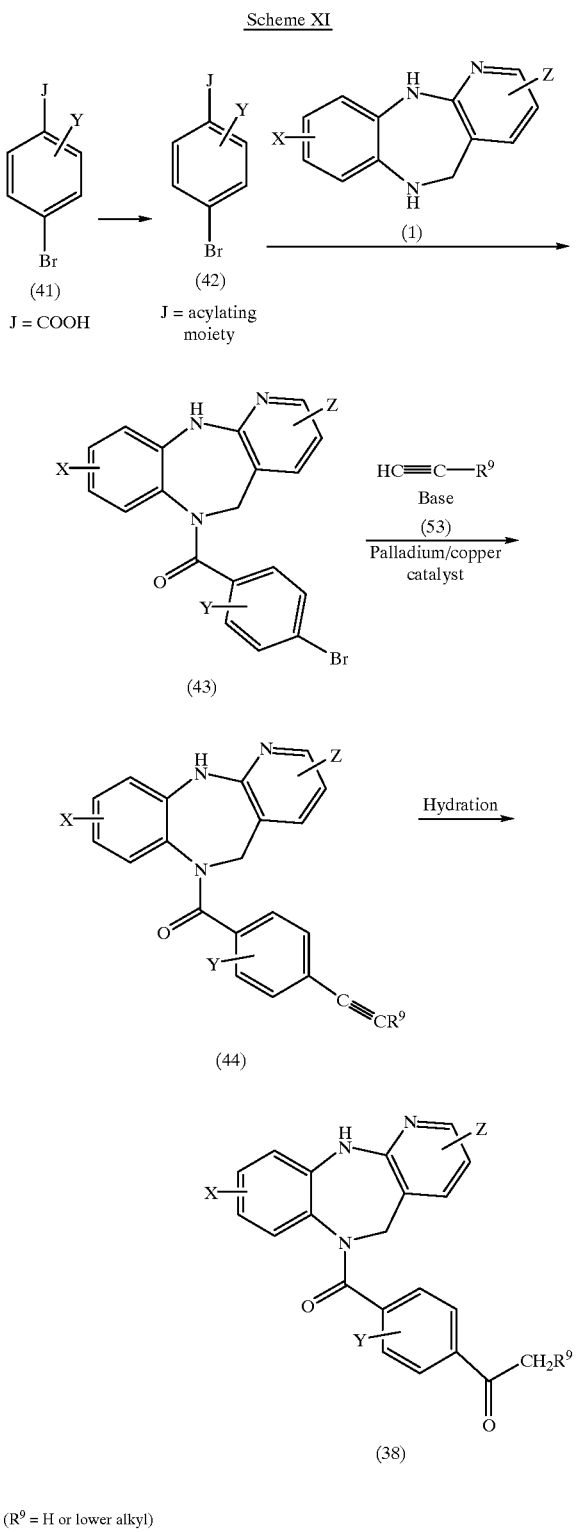

(R⁹ = H or lower alkyl)

Thus, a pyridobenzodiazepine of formula (1) is treated with an appropriately substituted bromoaroyl halide, preferably a bromoaroyl chloride of formula (42) according to any of the procedures described hereinbefore, to yield the acylated intermediate of formula (43). The intermediate (43) is subsequently coupled with a monosubstituted acetylene of formula (53, wherein $R^9$ is preferably trimethylsilyl, methyl or lower alkyl of 1 to 6 carbon atoms) in the presence of pyridine and a catalyst such as bis(triphenylphosphine) palladium (II) chloride and copper (I) iodide in an organic base such as triethylamine as the solvent, in a sealed pressure tube at temperatures ranging from ambient to 100° C. essentially according to the procedure of Martinez et al., *J. Med. Chem.*, 52, 3491 (1987). The resulting acetylene intermediate of formula (44) is then hydrated by treatment with 1% sulfuric acid in an aprotic organic solvent such as tetrahydrofuran saturated with mercury (II) sulfate at ambient temperature essentially according to the procedure of Reed et al, *J. Org. Chem.*, 52, 3491 (1987) to provide the desired acyl compound of formula (38) wherein X, Y, and Z are as defined above, and $R^9$ is hydrogen, or lower alkyl of 1 to 6 carbon atoms.

Alternatively, compound (44) where $R^9$ is trimethylsilyl is treated with n-tetrabutylammonium fluoride in an ether solvent such as tetrahydrofuran, to afford compound (44) where $R^9$ is hydrogen.

The preferred acylating agents of formula (42) of Scheme XI are conveniently prepared by treating an appropriately substituted aryl carboxylic acid of formula (41) with thionyl chloride at temperatures ranging from ambient to the reflux temperature of the solvent, or with oxalyl chloride in an aprotic solvent such as dichloromethane or tetrahydrofuran in the presence of a catalytic amount of dimethylformamide at temperatures ranging from 0° C. to 40° C.

The acetylene intermediates (53) of Scheme XI are either available commercially, or are known in the art, or can be readily prepared by procedures analogous to those in the literature for the known compounds.

As shown in Scheme XII, the intermediate acetyl compounds (38) of Scheme X can be prepared also by the Stille coupling of a bromo aryl compound of formula (43) of Scheme XI with an (α-alkoxyvinyl)trialkyltin preferably an (α-ethoxyvinyl)tributyltin of formula (45), in the presence of a catalytic amount of bis(triphenylphosphine) palladium (II) chloride in an aprotic organic solvent such as toluene at temperatures ranging from ambient to the reflux temperature of the solvent, essentially according to the procedure of Kosugi et al., *Bull. Chem. Soc. Jpn.*, 60, 767 (1987).

Scheme XII

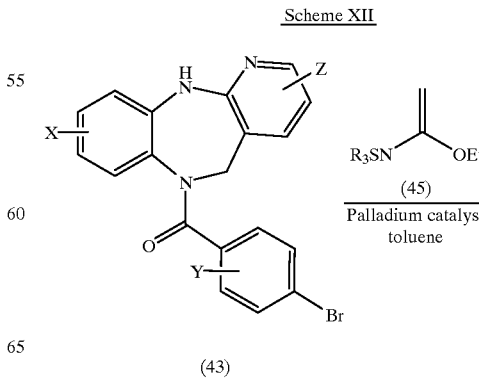

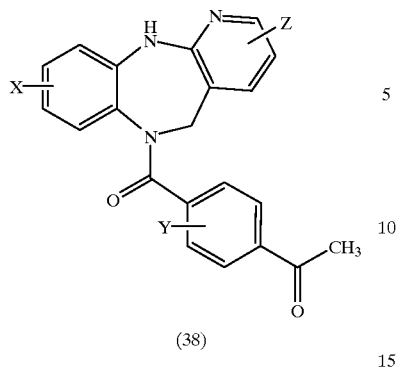

(38)

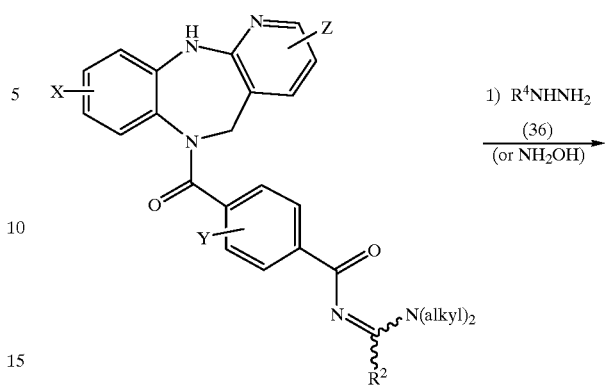

(48)

The preparation of the acetyl compound (38) can also be accomplished via the palladium-catalyzed arylation of a vinyl alkylether such as vinyl butylether, with the aryl halide intermediate of formula (43) according to the procedure of Cabri et al., *Tetrahedron Lett.*, 32, 1753 (1991).

The (α-alkoxyvinyl)trialkyltin intermediates (45) of Scheme XII are either available commercially, or are known in the art, or can be readily prepared by procedures analogous to those in the literature for the known compounds.

Compounds in which $R^1$ contains three heteroatoms are prepared according to Scheme XIII.

Scheme XIII

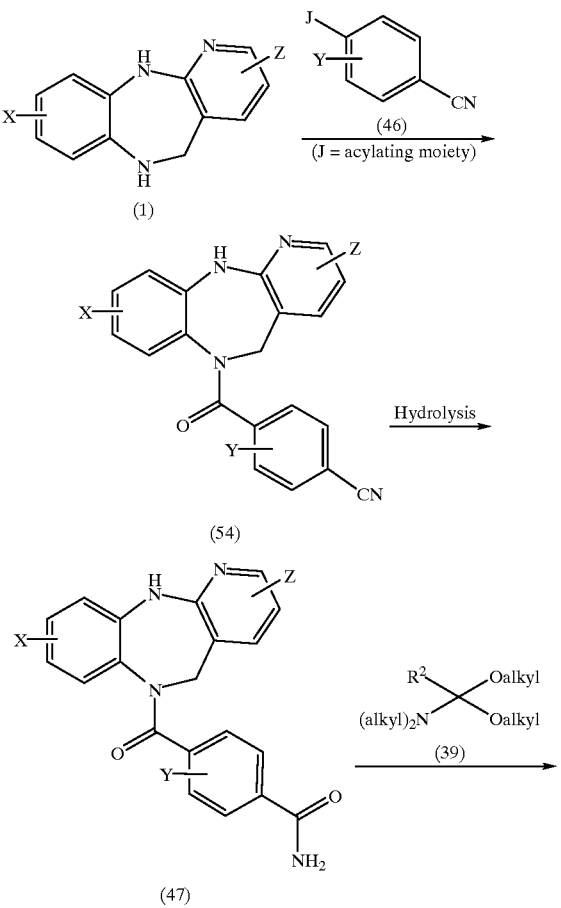

Thus, a pyridobenzodiazepine of formula (1) is treated with an appropriately substituted cyanoaroyl halide, preferably a cyanoaroyl chloride of formula (46) according to any of the procedures described hereinbefore, to yield an intermediate nitrile of formula (54) which, in turn, is converted to an amide intermediate of general formula (47) by treatment with an inorganic acid such as sulfuric acid at temperatures ranging from ambient to 50° C. Treatment of the amide (47) with a dialkylamide dialkylacetal such as a dimethylamide dimethylacetal of formula (39, wherein alkyl is $CH_3$) in an aprotic organic solvent such as dichloromethane or tetrahydrofuran at temperatures ranging from 0° C. to the reflux temperature of the solvent yields the intermediate of formula (48). Treatment of (48) with hydroxylamine or a hydrazine of formula (36) in acetic acid at temperatures ranging from ambient to reflux yields the desired target compounds of formula (I) wherein X, Y, Z, $R^2$ and $R^4$ are as defined above, and $R^1$ is an heterocyclic moiety selected from the (c), (g), or (i) group of heterocycles defined above and illustrated below.

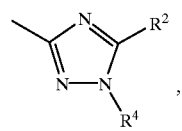

(c)

(g)

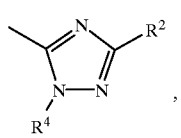

(i)

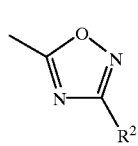

Another preferred process for the preparation of the intermediate amide of formula (47) of Scheme XIII is outlined in Scheme XIV. An appropriately substituted aryl nitrile of formula (49) is hydrated with basic hydrogen peroxide in dimethylsulfoxide essentially according to the procedure of Katritzky et al., *Synthesis*, 949 (1989), to provide the intermediate amide (50). Subsequent hydrolysis of the ester moiety gives the carboxylic acid intermediate (51) which is then converted into the acylating species of formula (52) by using any of the procedures described hereinbefore. Treatment of a pyridobenzodiazepine of formula (1) with (52) using any of the procedures described hereinbefore provides the desired intermediate amide (47).

Scheme XIV

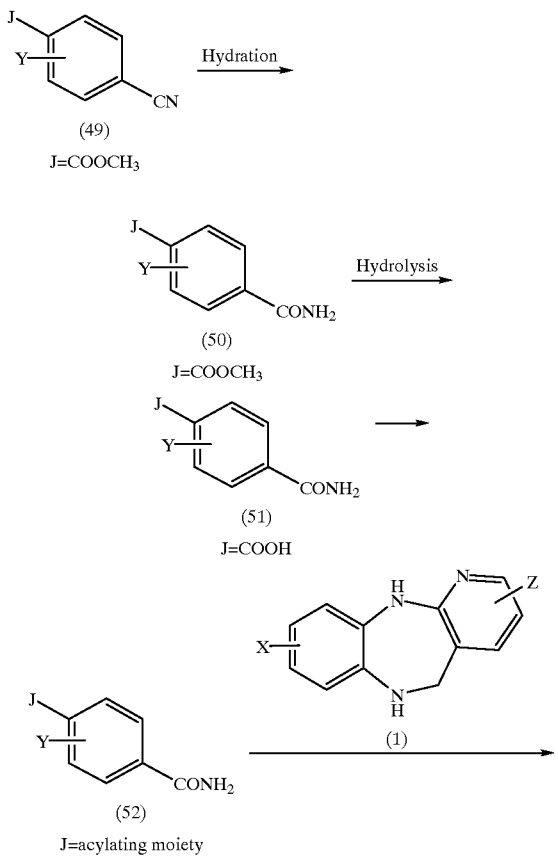

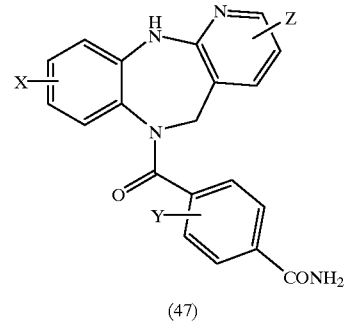

Another preferred process to prepare compounds of general formula (5) of Scheme XV where $R^1$ is an heterocyclic moiety selected from the c or g group of heterocycles defined above, and $R^4$ is not hydrogen, is shown in Scheme XV.

Scheme XV

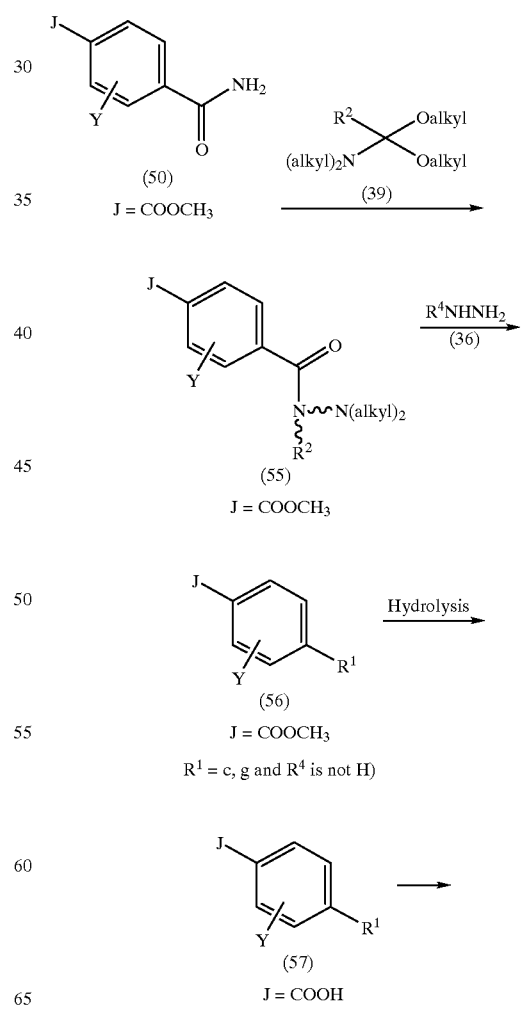

-continued

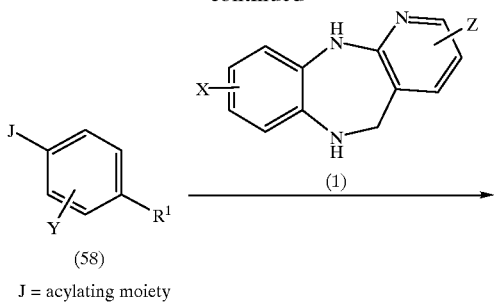

(58)

J = acylating moiety

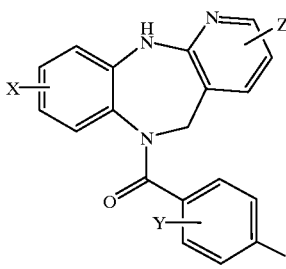

5, R¹ = c, g, and R⁴ is not H)

Thus, an appropriately substituted amide of formula (50) of Scheme XIV is treated with a dialkylamide dialkylacetal such as a dimethylamide dimethylacetal of formula (39, where alkyl is CH₃) at temperatures ranging from 0° C. to 100° C. to provide the intermediate of formula (55). Treatment of (55) with a substituted hydrazine of formula (36) in acetic acid at temperatures ranging from ambient to reflux, yields the desired intermediate triazole ester of formula (56). The ester (56) is subsequently hydrolyzed to the carboxylic acid of formula (57, wherein R¹ is an heterocyclic moiety selected from the (c) or (g) group of heterocycles defined above, and R⁴ is not hydrogen) which is then converted to an acylating agent, preferably an acid chloride or a mixed anhydride of formula (58) by procedures analogous to those described hereinbefore. The acylating species (58) is used to acylate a pyridobenzodiazepine of formula (1) to yield the desired compound of formula (5) wherein X, Y, Z and R² are as defined above, R¹ is an heterocyclic moiety selected from the (c) and (g) groups of heterocycles defined above and illustrated below, and R⁴ is not hydrogen.

(c)

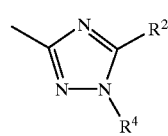

(g)

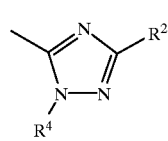

Alternatively, the compounds of general formula (5) of Scheme XIII wherein R¹ is an heterocyclic moiety selected from the (c) group of heterocycles defined above, and R⁴ is not hydrogen can be prepared as illustrated in Scheme XVI.

Scheme XVI

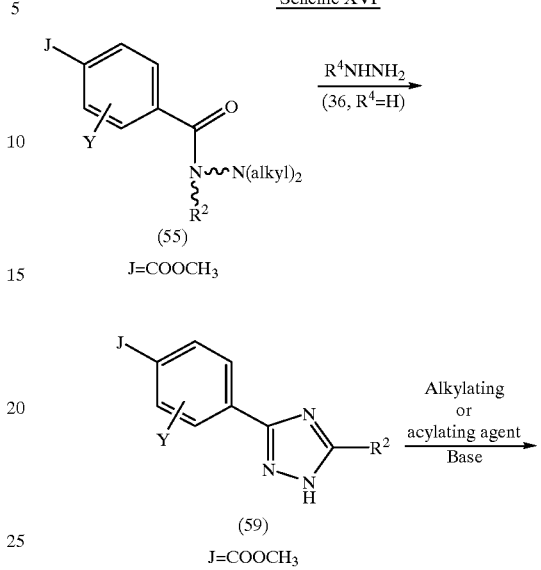

(55)

J=COOCH₃

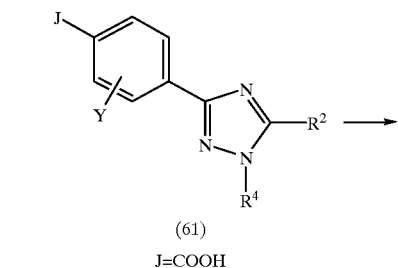

(59)

J=COOCH₃

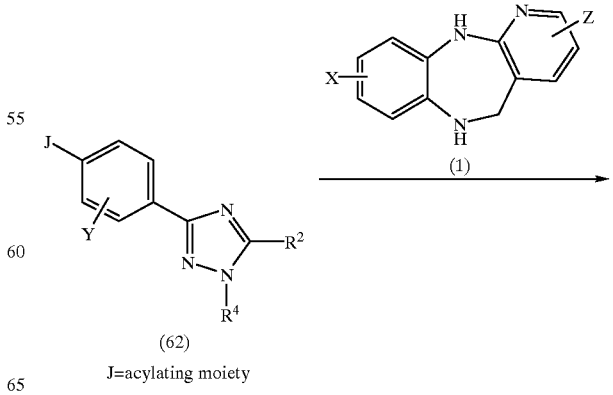

(60)

J=COOCH₃

(61)

J=COOH (62)

J=acylating moiety

-continued

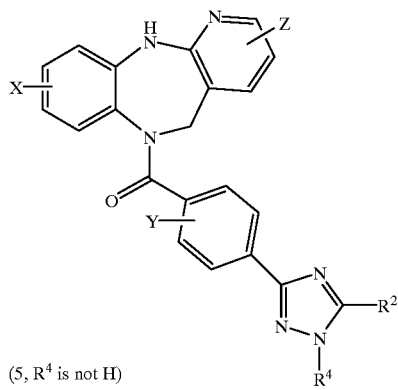

(5, R⁴ is not H)

Treatment of the intermediate ester of formula (55) of Scheme XV with an unsubstituted hydrazine (36, where R⁴ is H) in acetic acid at temperatures ranging from ambient to the reflux temperature, yields the intermediate triazole ester of formula (59). In this case the heterocyclic nitrogen can be alkylated or acylated by procedures analogous to those described hereinbefore, to yield the substituted triazole ester of formula (60). The ester (60) is subsequently hydrolyzed to the carboxylic acid of formula (61) which is then converted into an acylating species, preferably an acid chloride or mixed anhydride of formula (62), by procedures analogous to those described hereinbefore. The acylating agent (62) is used to acylate a pyridobenzodiazepine of formula (1) to yield the desired compound of formula (5) wherein X,Y, Z and R² are as defined above, R¹ is a heterocyclic moiety selected from the (c) group of heterocycles defined above, and R⁴ is not hydrogen.

Alternatively, a compound of general formula (5) of Scheme XIII wherein Y, Z and R² are as defined above, R¹ is an heterocyclic moiety selected from the (c) and (g) group of heterocycles defined above and illustrated below, and R⁴ is hydrogen, can be conveniently prepared from a compound of formula (5) of Scheme XVI wherein R⁴ is an optionally substituted aralkyl group, preferably a p-methoxybenzyl group by using a number of procedures which include hydrogenolysis or treatment with a strong acid such as trifluoroacetic acid at temperatures ranging from 0° C. to reflux temperature, essentially according to the procedure of Buckle et al., *J. Chem. Soc. Perkin Trans.* 1, 627 (1982).

(c)

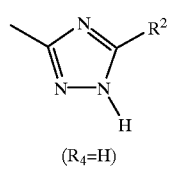

(R₄=H)

(g)

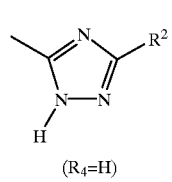

(R₄=H)

The preferred process to prepare compounds of general formula (5) in which R¹ contains four heteroatoms, and R⁴ is hydrogen is outlined in Scheme XVII.

Scheme XVII

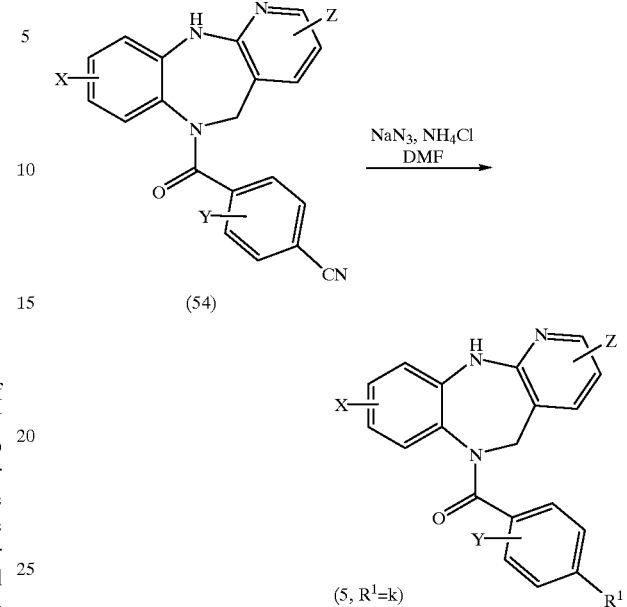

Treatment of the nitrile intermediate of formula (54) of Scheme XIII with sodium azide and ammonium chloride in an aprotic organic solvent such as dimethylformamide at temperatures ranging from ambient to the reflux temperature of the solvent, yields the desired compound of formula (5) wherein X, Y, and Z are as defined above, R¹ is an heterocyclic moiety selected from the (k) group of heterocycles defined above and illustrated below, and R⁴ is hydrogen.

(k)

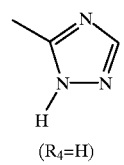

(R₄=H)

Alternatively, the compounds of formula (I) of Scheme I can be prepared according to the process outlined in Scheme XVIII.

Scheme XVIII

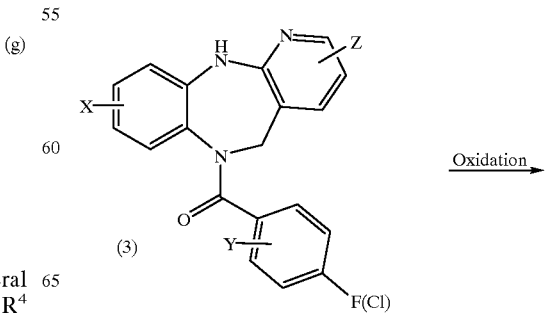

-continued

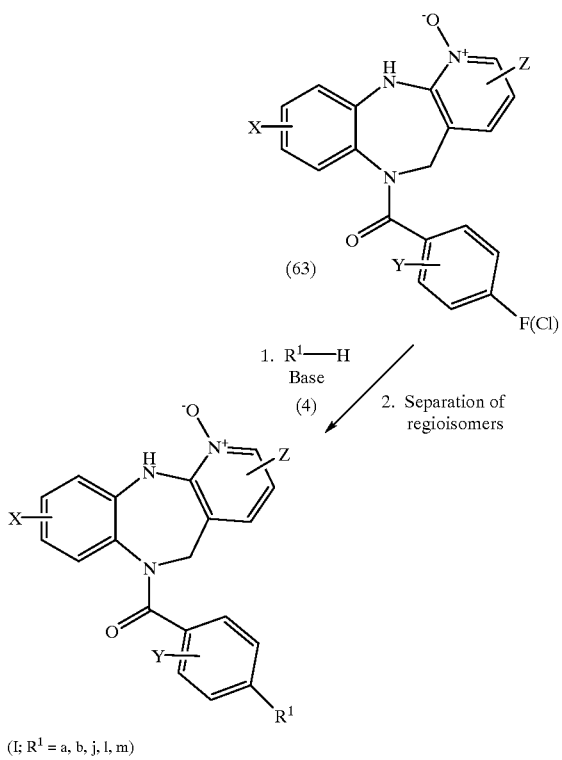

Thus, treatment of an acylated pyridobenzodiazepine intermediate of formula (3) of Scheme (I) with an oxidizing agent such as a peracid acid, methyltrioxorhenium-$H_2O_2$ or other pyridine oxidizing agents known in the literature (see Coperet et al., *J. Org. Chem.*, 63, 1740–1741 (1998) and references therein) at temperatures ranging from −40° C. to ambient temperature, provides a N-oxide intermediate of general formula (63) wherein X, Y, and Z are as defined above. Treatment of (63) with the sodium (potassium or lithium) salt of an appropriately substituted heterocycle of formula (4, wherein $R^1$ is an heterocyclic moiety selected from the (a), (b), (j), (l), and (m) groups of heterocycles defined above) in an aprotic organic solvent such as dimethylformamide (or tetrahydrofuran) at temperatures ranging from −40° C. to ambient, provides a compound of general formula (I) of Scheme I.

The subject compounds of the present invention were tested for biological activity according to the following procedures.

Vasopressin $V_2$ Agonist Effects of Test Compounds in Normal Conscious Water-Loaded Rats Male or female normotensive Sprague-Dawley rats (Charles River Laboratories, Inc., Kingston, N.Y.) of 350–500 g body weight were supplied with standard rodent diet (Purina Rodent Lab. Chow 5001) and water ad libitum. On the day of test, rats were placed individually into metabolic cages equipped with devices to separate the feces from the urine and containers for collection of urine. A test compound or a reference agent was given at an oral dose of 10 mg/kg in a volume of 10 ml/kg. The vehicle used was 20% dimethylsulfoxide (DMSO) in 2.5% preboiled corn starch. Thirty minutes after dosing the test compound, rats were gavaged with water at 30 ml/kg into the stomach using a feeding needle. During the test, rats were not provided with water or food. Urine was collected for four hours after dosing the test compound. At the end of four hours, urine volume was measured. Urinary osmolality was determined using a Fiske One-Ten Osmometer (Fiske Associates, Norwood, Mass., 02062) or an Advanced CRYOMATIC Osmometer, Model 3C2 (Advanced Instruments, Norwood, Mass.). Determinations of $Na^+$, $K^+$ and $Cl^-$ ion were carried out using ion specific electrodes in a Beckman SYNCHRON EL-ISE Electrolyte System analyzer. The urinary osmolality should increase proportionally. In the screening test, two rats were used for each compound. If the difference in the urine volume of the two rats was greater than 50%, a third rat was used.

The results of this study are shown in Table I.

TABLE 1

| Example | Urine Volume (% decrease)[a] | Changes in Urinary Osmolality[b] | Rat Type[c] |
|---|---|---|---|
| 1 | 80 | 753 | CD |
| 3 | 90 | 747 | CD |
| 4 | 72 | 331 | CD |

[a]Percent decrease in urine volume vs. control at a dose of 10 mg/kg
[b]Percent changes in osmolality vs. control at a dose of 10 mg/kg
[c]Rat model used: Sprague-Dawley (CD)

The following examples are presented to illustrate rather than limit the scope of this invention.

EXAMPLE 1

[2-Chloro-4-(3-methyl-1H-pyrazol-1-yl)-phenyl]-(6,11-dihydro-5H-pyrido[2,3-b][1,5]benzodiazepin-6-yl)-methanone-1-oxide Step A. 6,11-Dihydro-5H-pyrido[2,3-b][1,5] benzodiazepin-5-one 1:1 salt with hydrochloric acid A mixture of 1,2-phenylene diamine (52 g, 480 mmol) and chloro nicotinic acid (76 g, 482 mmol) in cyclohexanol (480 mL) was refluxed under nitrogen for 2.5 hours. A precipitate appeared soon after the heating was initiated. The warm reaction mixture was carefully poured onto ice-cold dichloromethane (1000 mL) under vigorous stirring. The semisolid mass was collected, washed thoroughly with dichloromethane and dried in vacuo to yield 98.9 g of the title compound which was used in the next step without further purification.

Step B. 6,11-Dihydro-5H-pyrido[2,3-b][1,5] benzodiazepine

Diborane dimethylsulfide complex (35 mL) was added via syringe to a suspension of 6,11-dihydro-5H-pyrido[2,3-b][1,5]benzodiazepin-5-one 1:1 salt with hydrochloric acid of Step A (25 g, 0.1 mole) in dioxane (230 mL) under nitrogen. The mixture was sonicated overnight at room temperature and then evaporated to dryness in vacuo. The green residue was treated with cold 2N hydrochloric acid and diethyl ether. The cold aqueous layer was basified with 50% aqueous sodium hydroxide (to pH 9) and the basic layer extracted with ethyl acetate. The organic extracts were dried over anhydrous potassium carbonate, and evaporated to dryness to yield a burgundy solid (24.35 g). This crude material was purified by trituration with diethyl ether. The solid was collected, washed and dried in vacuo. The mother liquors from different runs were combined and the mixture (18.5 g) flash chromatographed (on silica Merck-60, eluant 20% ethyl acetate in hexane) to provide additional material homogeneous by TLC (yellow solid, 11 g).

Step C. 2-Chloro-4-fluorobenzoyl chloride

A suspension of the 2-chloro-4-fluorobenzoic acid (13.61 g, 78 mmol) in dichloromethane (85 mL) containing a few drops of dimethylformamide was treated dropwise under nitrogen with a 2M solution of oxalyl chloride in dichloromethane (1.2 equivalents). After gas evolution subsided, the reaction mixture was refluxed for an additional 25 minutes and then evaporated to dryness in vacuo. The crude acid chloride was used as such in the next step.

Step D. (2-Chloro-4-fluorophenyl)-(6,11-dihydro-5H-pyrido[2,3-b][1,5]benzodiazepin-6-yl)-methanone To a solution of 6,11-dihydro-5H-pyrido[2,3-b][1,5]benzodiazepine of Step B (12.8 g, 65 mmol) in dimethylformamide (120 mL) under nitrogen was added potassium carbonate (19.76 g, 143 mmol). The mixture was cooled and treated dropwise with a solution of crude 2-chloro-4-fluorobenzoyl chloride of Step C (78 mmol) in dimethylformamide (50 mL). After stirring at room temperature for 75 minutes the mixture was diluted with water and extracted with dichloromethane. The organic extracts were dried over magnesium sulfate and evaporated to dryness. The crude material was purified by flash chromatography (on silica Merck-60, hexane-ethyl acetate gradient from 95:5 to 80:20) to provide the pure title compound (14.25 g) along with some less pure material (2.7 g). The pure material is an off-white crystalline solid, which is used as such in the next step.

NMR (DMSO-$d_6$, 400 MHz): δ 4.13 and 5.42 (dd, 2H), 6.52 (m, 1H), 6.71–6.79 (m, 2H), 6.98–7.16 (m, 2H), 7.23–7.33 (m, 3H), 7.58 (m, 1H), 8.10 (m, 1H), 9.53 (s, 1H)

MS (EI, m/z): 353/355 [M]$^+$, 196

Step E. [2-Chloro-4-(3-methyl-1H-pyrazol-1-yl)-phenyl]-(6,11-dihydro-5H-pyrido[2,3-b][1,5]benzodiazepin-6-yl)-methanone Sodium hydride (60% suspension in oil, 1.8 g, 45.19 mmol) was washed with hexane, dried under nitrogen and resuspended in dry dimethylformamide (130 mL). Neat 3-methyl pyrazole (3.71 g, 45.19 mmol) was added dropwise at 0° C. After the gas evolution subsided the cooling bath was removed and stirring was continued at room temperature. The (2-chloro-4-fluorophenyl)-(6,11-dihydro-5H-pyrido[2,3-b][1,5]benzodiazepin-6-yl)-methanone of Step D (8.11 g, 22.59 mmol) was added in one portion and the mixture was placed in an oil bath (preheated at 130° C.) for 2 hrs. After cooling, the mixture was partitioned between water and ethyl acetate. The organic extracts were dried over sodium sulfate, and evaporated to dryness in vacuo. The residue was dissolved in dichloromethane and absorbed onto a silica Merck-60 flash column. Elution with a hexane-ethyl acetate gradient (from 95:5 to 3:2) provided the desired product along with some mixed fractions containing the title compound and its more polar 5-methylpyrazole regioisomer of Example 2. The title compound crystallized by sonication from hexane-ethanol as a white solid (6.4 g), m.p. 207° C.

NMR (DMSO-$d_6$, 400 MHz): δ2.21 (s, 3H), 4.14 and 5.45 (dd, 2H), 6.32 (m, 1H), 6.51 (m, 1H), 6.74–6.79 (m, 2H), 6.98 (m, 1H), 7.25 (m, 2H), 7.58–7.70 (m, 3H), 8.11 (m, 1H), 8.38 (m, 1H), 9.55 (s, 1H)

MS (EI, m/z): 415/417 [M]$^+$; (+FAB, m/z): 416/418 [M+H]$^+$

Anal. Calc'd for $C_{23}H_{18}ClN_5O$: C 66.43; H4.36; N 16.84. Found: C 66.11; H4.42; N 16.64.

Step F. [2-Chloro-4-(3-methyl-1H-pyrazol-1-yl)-phenyl]-(6,11-dihydro-5H-pyrido[2,3-b][1,5]benzodiazepin-6-yl)-methanone 1-oxide 0.09 solvate with ethanol To a solution of [2-chloro-4-(3-methyl-1H-pyrazol-1-yl)-phenyl]-(6,11-dihydro-5H-pyrido[2,3-b][1,5]benzodiazepin-6-yl)-methanone of Step E (1.1 g, 2.64 mmol) at 0° C. was added meta-chloroperbenzoic acid (0.53 g, 2.76 mmol). The mixture was allowed to warm to room temperature and after 90 minutes quenched by addition of aqueous NaHSO$_3$. The organic layer was separated and washed with saturated aqueous sodium bicarbonate and water, and dried over sodium sulfate. Evaporation of the solvent provided a yellow solid that was redissolved in dichloromethane and absorbed onto a flash column of silica Merck-60. Elution with 2% methanol in dichloromethane provided the title compound as a white foam which crystallized from ethanol to yield a white solid (0.97 g, m.p. 255–257° C.).

NMR (DMSO-$d_6$, 400 MHz): δ2.21 (s, 3H), 4.30 and 5.59 (dd, 2H), 6.32 (m, 1H), 6.69 (m, 1H), 6.82–6.90 (m, 2H), 7.09 (m, 1H), 7.37 (m, 1H), 7.49 (m, 3H), 7.64–7.71 (m, 2H), 8.27 (m, 1H), 8.38 (m, 1H), 9.99 (s, 1H)

MS [EI, m/z]: 431 [M]$^+$

Anal. Cald. for $C_{23}H_{18}ClN_5O_2$+0.09 $C_2H_5OH$: C 63.85; H 4.29; N 16.06. Found: C 63.45, H 4.58, N 16.18.

EXAMPLE 2

[2-Chloro-4-(5-methyl-1H-pyrazol-1-yl)-phenyl]-(6,11-dihydro-5H-pyrido[2,3-b][1,5]benzodiazepin-6-yl)-methanone-1-oxide Step A. [2-Chloro-4-(5-methyl-1H-pyrazol-1-yl)-phenyl]-(6,11-dihydro-5H-pyrido[2,3-b][1,5]benzodiazepin-6-yl)-methanone The fractions (0.543 g) containing a mixture of 3-methyl and 5-methylpyrazole regioisomers obtained as described in Example 1, Step E were subjected to flash chromatography (silica gel Merck-60, eluant: toluene-ethyl acetate 90:10 followed by toluene-ethyl acetate-acetonitrile 90:10:5) to provide 0.327 g of the already described 3-methyl isomer of example 1, and 0.105 g of the title compound as an amorphous solid upon sonication from ether-hexane.

NMR (DMSO-$d_6$, 400 MHz): δ2.27 (s, 3H), 4.16 and 5.45 (dd, 2H), 6.25 (m, 1H), 6.54 (m, 1H), 6.79 (m, 2H), 7.01 (m, 1H), 7.26 (m, 1H), 7.40–7.54 (m, 3H), 7.61 (m,2H), 8.11 (m, 1H), 9.56 (s, 1H)

MS [EI, m/z]: 415/417 [M]$^+$, 219/221, 196

Step B. [2-Chloro-4-(5-methyl-1H-pyrazol-1-yl)-phenyl]-(6,11-dihydro-5H-pyrido[2,3-b][1,5]benzodiazepin-6-yl)-methanone-1-oxide Prepared by treatment of [2-chloro-4-(5-methyl-1H-pyrazol-1-yl)-phenyl]-(6,11-dihydro-5H-pyrido[2.3-b][1.5]benzodiazepin-6-yl)-methanone of Step A with meta-chloro perbenzoic acid in the manner of Example 1, Step F.

EXAMPLE 3

[2-Bromo-4-(3-methyl-1H-pyrazol-1-yl)-phenyl]-(6,11-dihydro-5H-pyrido[2,3-b][1,5]benzodiazepin-6-yl)-methanone-1-oxide Step A. 2-Bromo-4-fluorobenzoyl chloride A suspension of 2-bromo-4-fluorobenzoic acid (6.87 g, 31.37 mmol) in dichloromethane (70 mL) containing a few drops of dimethylformamide was treated dropwise under nitrogen with a 2M solution of oxalyl chloride in dichloromethane (1.16 equivalents). After gas evolution subsided, the reaction mixture was refluxed for an additional 25 minutes and then the solution was evaporated to dryness in vacuo. The crude acid chloride was used as such in the next step.

Step B. [2-Bromo-4-fluorophenyl]-(6,11-dihydro-5H-pyrido[2,3-b][1,5]benzodiazepin-6-yl)-methanone To a solution of 6,11-dihydro-5H-pyrido[2,3-b][1,5] benzodiazepine of Example 1, Step B (5.15 g, 26.1 mmol) in dimethylformamide (70 mL) under nitrogen was added potassium carbonate (7.95 g, 57.51 mmol). The mixture was cooled and treated dropwise with a solution of crude 2-bromo-4-fluorobenzoyl chloride of Step A (31.37 mmol) in dimethylformamide (30 mL). After stirring at room temperature for 75 minutes the mixture was diluted with water and extracted with dichloromethane. The organic extracts were dried over magnesium sulfate and evaporated to dryness to give a brown solid foam. The crude material was dissolved in dichloromethane and absorbed onto a silica Merck-60 flash column. Elution with a hexane-ethyl acetate gradient (from 95:5 to 75:25) provided the pure title compound (6.18 g) along with some impure material (1.2 g). The pure material was triturated with hexane to provide an off-white solid foam, which was used as such in the next step.

NMR (DMSO-$d_6$, 400 MHz): δ4.13 and 5.42 (dd, 2H), 6.53 (m, 1H), 6.74–6.79 (m, 2H), 6.98–7.16 (m, 3H), 7.25 (m, 1H), 7.40–7.50 (broad s, 1H), 7.59 (m, 1H), 8.1 (m, 1H), 9.54 (s, 1H)

MS (EI, m/z): 397/399 [M]$^+$, 196

Step C. [2-Bromo-4-(3-methyl-1H-pyrazol-1-yl)-phenyl]-(6,11-dihydro-5H-pyrido[2,3-b][1,5]benzodiazepin-6-yl)-methanone Sodium hydride (60% suspension in oil, 1.2 g, 30.15 mmol) was washed with hexane, dried under nitrogen and resuspended in dry dimethylformamide (110 mL). Neat 3-methylpyrazole (2.47 g, 30.15 mmol) was added dropwise at 0° C. After the gas evolution subsided the cooling bath was removed and stirring was continued at room temperature. The [2-bromo-4-fluorophenyl]-(6,11-dihydro-5H-pyrido[2,3-b][1,5]benzodiazepin-6-yl)-methanone of Step B (6 g, 18.07 mmol) was added in one portion to the clear solution. The mixture was placed in an oil bath (preheated at 130° C.) for 40 minutes, cooled and partitioned between water and ethyl acetate. The organic extracts were dried over magnesium sulfate and evaporated to dryness. The crude material was dissolved in dichloromethane and absorbed onto a silica Merck-60 flash column. Elution with a hexane-ethyl acetate gradient (from 95:5 to 75:25) provided the less polar title compound (3.87 g) along with a mixture of 3- and 5-methylpyrazole regioisomers (0.860 g). The title compound (3.5 g) crystallized by sonication from hexane-ethanol, m.p. 208–209° C. (dec).

NMR (DMSO-$d_6$, 400 MHz): δ2.21 (s, 3H), 4.15 and 5.44 (dd, 2H), 6.31 (m, 1H), 6.52 (m, 1H), 6.77–6.80 (m, 2H), 6.99 (m, 1H), 7.25 (m, 1H), 7.59–7.63 (2 m, 2H), 7.88 (m, 1H), 8.11 (m, 1H), 8.37 (s, 1H), 9.55 (s, 1H)

MS (+EI, m/z): 459/461 [M]$^+$, 265/263

Anal. Calc'd for $C_{23}H_{18}BrN_5O$: C 60.01, H 3.94, N 15.21. Found: C 59.92, H 4.05, N 15.01.

Step D. [2-Bromo-4-(3-methyl-1H-pyrazol-1-yl)-phenyl]-(6,11-dihydro-5H-pyrido[2,3-b][1,5]benzodiazepin-6-yl)-methanone-1-oxide To a solution of [2-bromo-4-(3-methyl-1H-pyrazol-1-yl)-phenyl]-(6,11-dihydro-5H-pyrido[2,3-b][1,5] benzodiazepin-6-yl)-methanone of Step C (1 g, 2.2 mmol) at 0° C. was added meta-chloroperbenzoic acid (0.44 g, 2.3 mmol). The reaction mixture was allowed to warm to room temperature, stirred for 90 minutes and quenched with aqueous $NaHSO_3$. The organic layer was separated and washed with saturated aqueous sodium bicarbonate and water, and dried over sodium sulfate. Removal of the solvent provided a yellow solid which was redissolved in dichloromethane and absorbed onto a flash column of silica Merck-60. Elution with 2% methanol in dichloromethane provided the title compound as a white foam which crystallized from diethyl ether to yield a white solid (0.68 g, m.p. >260° C.).

NMR (DMSO-$d_6$, 400 MHz): δ2.21 (s, 3H), 4.30 and 5.58 (dd, 2H), 6.32 (m, 1H), 6.70 (m, 1H), 6.84 (m, 1H), 6.91 (m, 1H), 7.09 (m, 1H), 7.37 (m, 1H), 7.49 (m, 1H), 7.67 (m, 1H), 7.88 (m, 1H), 8.11 (m, 1H), 8.27 (s, 1H), 8.38 (m, 1H), 9.99 (s, 1H)

MS (+EI, m/z): 475 [M]$^+$

Anal. Calc'd for $C_{23}H_{18}BrN_5O_2$: C 58.00, H 3.81, N 14.70. Found: C 57.76, H 3.86, N 14.50.

EXAMPLE 4

4-[(3-Methyl-1H-pyrazol-1-yl)-2-(trifluoromethyl)-phenyl]-(6,11-dihydro-5H-pyrido[2,3-b][1,5]benzodiazepin-6-yl)-methanone 1-oxide

Step A. 2-Trifluoromethyl-4-fluorobenzoyl chloride

A suspension of 2-trifluoromethyl-4-fluorobenzoic acid (16.85 g, 81 mmol) in dichloromethane (150 mL) containing a few drops of dimethylformamide was treated dropwise under nitrogen with oxalyl chloride (8.5 mL, 97.4 mmol). After the gas evolution subsided, the reaction mixture was refluxed for an additional 10 minutes, and then evaporated to dryness in vacuo. The crude acid chloride was used as such in the next step.

Step B. (6,11-Dihydro-5H-pyrido[2,3-b][1,5]benzodiazepin-6-yl)-(4-fluoro-2-trifluoromethyl-phenyl)-methanone To a solution of 6,11-dihydro-5H-pyrido[2,3-b][1,5] benzodiazepine of Example 1, Step B (10.6 g, 53.8 mmol) in dimethylformamide (125 mL) under nitrogen was added potassium carbonate (22.4 g, 162 mmol). The mixture was cooled and treated dropwise with a solution of crude 2-trifluoromethyl-4-fluorobenzoyl chloride of Step A (81 mmol) in dimethylformamide (25 mL). After stirring at room temperature for 2 hours, the mixture was diluted with water and extracted with dichloromethane. The organic extracts were dried over magnesium sulfate and evaporated to dryness. The crude material was dissolved in dichloromethane and purified by flash chromatography (on silica Merck-60, hexane-ethyl acetate 80:20) to provide the pure title compound (6.9 g) which was crystallized by sonication from ethanol-hexane, m.p. 183–185° C.

NMR (DMSO-$d_6$, 400 MHz) δ4.16 and 5.43 (dd, 2H), 6.56 (m, 1H), 6.64 (m, 1H), 6.79 (m, 1H), 7.02 (m, 1H), 7.26–7.40 (m, 3H), 7.58–7.65 (m, 2H), 8.12 (m, 1H), 9.59 (s, 1H)

MS (EI, m/z): 387 [M]$^+$

Anal. Calc'd for $C_{20}H_{13}F_4N_3O$: C 62.02, H 3.38, N 10.85. Found: C 62.06, H 3.22, N 10.67.

Step C. [4-(3-Methyl-1H-pyrazol-1-yl)-2-(trifluoromethyl)-phenyl]-(6,11-dihydro-5H-pyrido[2,3-b][1,5]benzodiazepin-6-yl)-methanone Sodium hydride (60% suspension in oil, 0.83 g, 20.8 mmol) was washed once with hexane, dried under nitrogen and resuspended in dry dimethylformamide (60 mL). 3-methyl pyrazole (0.90 mL, 11.2 mmol) was added in one portion. After the gas evolution subsided the stirring was continued at room temperature. The (6,11-dihydro-5H-pyrido[2,3-b][1,5]benzodiazepin-6-yl)-(4-fluoro-2-trifluoromethylphenyl)-methanone of Step B (3.6 g, 9.3 mmol) was added in one portion and the mixture was placed in an oil bath (preheated at 130° C.) for 30 minutes. After cooling, the mixture was partitioned between water and ethyl acetate. The organic extracts were dried over sodium sulfate, and evaporated to dryness. The residue was dissolved in dichloromethane and absorbed onto a silica Merck-60 flash column. Elution with 25% ethyl acetate in hexane provided 3.3 g of the desired product as a foam which crystallized by sonication from ethanol-hexane, m.p. 212–214° C. Further elution with 30% ethyl acetate in hexane yielded the more polar 5-methylpyrazole regioisomer of Example 6.

NMR (DMSO-$d_6$, 400 MHz): δ2.23 (s, 3H), 4.17 and 5.45 (dd, 2H), 6.35 (m, 1H), 6.54 (m, 1H), 6.68 (m, 1H), 6.80 (m, 1H), 7.00 (m, 1H), 7.29 (m, 1H), 7.60 (m, 1H), 7.85 (m, 1H), 8.04 (m, 1H), 8.13 (m, 1H), 8.46 (m, 1H), 9.61 (s, 1H)

MS (EI, m/z): 449 [M]$^+$

Anal. Calc'd for $C_{24}H_{18}F_3N_5O$: C 64.14, H 4.04, N 15.58. Found: C 64.01, H 4.01, N 15.45.

Step D. 4-[(3-Methyl-1H-pyrazol-1-yl)-2-(trifluoromethyl)-phenyl]-(6,11-dihydro-5H-pyrido[2,3-b][1,5]benzodiazepin-6-yl)-methanone-1-oxide To a solution of [4-(3-methyl-1H-pyrazol-1-yl)-2-(trifluoromethyl)-phenyl]-(6,11-dihydro-5H-pyrido[2,3-b][1,5]benzodiazepin-6-yl)-methanone of Step C (1.1 g, 2.4 mmol) at 0° C. was added meta-chloroperbenzoic acid (0.50 g, 2.6 mmol). The reaction was allowed to warm to room temperature, stirred for 3 hours and quenched with aqueous NaHSO$_3$. The organic layer was separated, washed with saturated aqueous sodium bicarbonate and water, and dried over sodium sulfate. Removal of the solvent afforded a yellow solid that was redissolved in dichloromethane and absorbed onto a flash column of silica Merck-60. Elution with 2% methanol in dichloromethane provided the title compound as a white foam which crystallized from diethyl ether to yield a white solid (1 g, m.p. 233–235° C.).

EXAMPLE 5

[4-(3-Methyl-1H-pyrazol-1-yl)-2-(trifluoromethy)l-phenyl]-(6,11-dihydro-5H-pyrido[2,3-b][1,5]benzodiazepin-6-yl)-methanone Step A. 4-Fluoro-2-trifluoromethylbenzoic acid methyl ester A suspension of 4-fluoro-2-trifluoromethylbenzoic acid (25.6 g, 123.0 mmol) in dichloromethane (250 mL) containing a few drops of dimethylformamide was treated dropwise under nitrogen with oxalyl chloride (11.3 mL, 129.5 mmol). After the gas evolution subsided, the reaction mixture was refluxed for an additional 15 minutes. The mixture was cooled and methanol (50 mL) was added. After stirring for 2 hrs, the reaction was concentrated, and the residue was partitioned between dichloromethane and water. The organic phase was washed with saturated aqueous sodium bicarbonate, dried over sodium sulfate, and evaporated to dryness to give 18.0 g of the title compound as a golden oil.

NMR (DMSO-$d_6$, 400 MHz): δ3.85 (s, 3H), 7.67 (m, 1H), 7.80 (m, 1H), 7.95 (m, 1H) MS (EI, m/z): 222 [M]$^+$

The aqueous layer was acidified with 2 N hydrochloric acid and the white solid was collected by filtration to give 7.5 g of the starting 4-fluoro-2-trifluoromethylbenzoic acid.

Step B. 4-(3-Methyl-1H-pyrazol-1-yl)-2-(trifluoromethyl)-benzoic acid methyl ester Sodium hydride (60% suspension in oil, 3.85 g, 96.3 mmol) was washed with hexane, dried under nitrogen and resuspended in dry dimethylformamide (150 mL). A solution of 3-methylpyrazole (7.75 mL, 96.3 mmol) in dimethylformamide (50 mL) was added dropwise at ambient temperature. Stirring was continued until the gas evolution subsided, and then a solution of methyl 4-fluoro-2-trifluoromethylbenzoic acid methyl ester of Step A (17.8 g, 80.1 mmol) in dimethylformamide (50 mL) was added dropwise to the clear solution. After stirring for 30 min at room temperature, the reaction was quenched with saturated aqueous ammonium chloride and extracted with ethyl acetate. The organic extracts were dried over sodium sulfate and evaporated to dryness. The residue was dissolved in 1:1 mixture of dichloromethane and hexane and absorbed onto a silica Merck-60 flash column. Elution with a dichloromethane-hexane gradient (from 1:1 to 4:1) provided the title compound (13.6 g) as a white solid, m.p. 59–61° C.

NMR (DMSO-$d_6$, 400 MHz): δ2.28 (s, 3H), 3.86 (s, 3H), 6.43 (m, 1H), 7.97 (m, 1H), 8.18 (m, 1H), 8.23 (m, 1H), 8.62 (m, 1H)

MS (EI, m/z): 284 [M]$^+$

Anal. Calc'd for $C_{13}H_{11}F_3N_2O_2$: C 54.93, H 3.90, N 9.86. Found: C 54.80, H 3.73 N 9.81.

Step C. 4-(3-Methyl-1H-pyrazol-1-yl)-2-(trifluoromethyl)-benzoic acid

To a solution of 4-(3-methyl-1H-pyrazol-1-yl)-2-trifluoromethyl benzoic acid methyl ester of Step B (1.19 g, 4.2 mmol) in methanol (10 mL) was added 2.5 N sodium hydroxide (3.3 mL, 8.3 mmol). The mixture was heated at reflux for 90 minutes, cooled and concentrated. The residue was partitioned between ethyl acetate and 1N hydrochloric acid. The organic extracts were dried over sodium sulfate and evaporated to dryness to give the title compound (1.14 g) as a white solid, m.p. 192–194° C.

NMR (DMSO-$d_6$, 400 MHz): δ2.28 (s, 3H), 6.42 (m, 1H), 7.95 (m, 1H), 8.14 (m, 1H), 8.20 (m, 1H), 8.61 (m, 1H), 13.4–13.7 (broad s, 1H)

MS (+FAB, m/z): 271 [M+H]$^+$

Anal. Calc'd for $C_{12}H_9F_3N_2O_2$: C 53.34, H 3.36, N 10.37. Found: C 53.35, H 3.29, N 10.21.

Step D. [4-(3-Methyl-1H-pyrazol-1-yl)-2-(trifluoromethyl)-phenyl]-(6,11-dihydro-5H-pyrido[2,3-b][1,5]benzodiazepin-6-yl)-methanone To a solution of 4-(3-methyl-1H-pyrazol-1-yl)-2-trifluoromethyl benzoic acid (1.1 g, 4.1 mmole) of Step C, and triethylamine (0.57 mL, 4.1 mmol) in dichloromethane (20 mL) was added 2,4,6-trichlorobenzoyl chloride (0.63 mL, 4.0 mmol). After stirring for 5.5 hours, 6,11-dihydro-5H-pyrido[2,3-b][1,5]benzodiazepine of Example 1, Step B (0.67 g, 3.4 mmol) and 4-dimethylamino pyridine (0.42 g, 3.4 mmol) were added. After stirring for an additional 18 hours, the mixture was poured into saturated aqueous sodium bicarbonate. The organic phase was washed with brine, dried over sodium sulfate, and evaporated to dryness. The residue was dissolved in dichloromethane and absorbed onto a silica Merck-60 flash column. Elution with hexane-ethyl acetate (gradient from 8:2 to 7:3) provided the title product (0.89 g) as a foam which crystallized by sonication from ethanol-hexane, m.p. 212–214° C. This material was identical to the compound of Example 4, Step C.

EXAMPLE 6

[4-(5-Methyl-1H-pyrazol-1-yl)-2-(trifluoromethyl)-phenyl]-(6,11-dihydro-5H-pyrido[2,3-b][1,5]benzodiazepin-6-yl)-methanone-1-oxide Step A. [4-(5-Methyl-1H-pyrazol-1-yl)-2-(trifluoromethyl)-phenyl]-(6,11-dihydro-5H-pyrido[2,3-b][1,5]benzodiazepin-6-yl)-methanone solvate with 0.09 dichloromethane and 0.13 ethyl acetate The title compound (0.350 g) was obtained as described in Example 4 above, as a foam which crystallized by sonication from ethanol-hexane, m.p. 238–240° C.

NMR (DMSO-$d_6$, 400 MHz):δ2.29 (s, 3H), 4.19 and 5.46 (dd, 2H), 6.28 (m, 1H), 6.57 (m, 1H), 6.71 (m, 1H), 6.80 (m, 1H), 7.02 (m, 1H), 7.29 (m, 1H), 7.58–7.67 (m, 4H), 7.81 (m, 1H), 8.13 (m, 1H), 9.63 (s, 1H)

MS (+FAB, m/z): 450 [M+H]$^+$

Anal. Calc'd for $C_{24}H_{18}F_3N_5O+0.09$ $CH_2Cl_2+0.13$ $C_4H_8O_2$: C 63.09, H 4.13, N 14.95. Found: C 63.39, H 4.23, N 14.89.

Step B. [4-(5-Methyl-1H-pyrazol-1-yl)-2-(trifluoromethyl)-phenyl]-(6,11-dihydro-5H-pyrido[2,3-b][1,5]benzodiazepin-6-yl)-methanone-1-oxide Prepared by treatment of [4-(5-methyl-1H-pyrazol-1-yl)-2-(trifluoromethyl)-phenyl]-(6,11-dihydro-5H-pyrido[2,3-b][1,5]benzodiazepin-6-yl)-methanone of Step A with meta-chloro perbenzoic acid in the manner of Example 4, Step D.

EXAMPLE 7

[2-(Trifluoromethyl)-4-(3-(trifluoromethyl)-1H-pyrazol-1-yl)-phenyl]-(6,11-dihydro-5H-pyrido[2,3-b][1,5]benzodiazepin-6-yl)-methanone-1-oxide Step A. [2-(Trifluoromethyl)-4-(3-trifluoromethyl-1H-pyrazol-1-yl)-phenyl]-(6,11-dihydro-5H-pyrido[2,3-b][1,5]benzodiazepin-6-yl)-methanone Sodium hydride (60% suspension in oil, 0.17 g, 4.25 mmol) was washed with hexane, dried under nitrogen and resuspended in dry dimethylformamide (10 mL). 3-trifluoromethyl pyrazole (0.34 g, 2.5 mmol) was added in one portion. After the gas evolution subsided stirring was continued at room temperature. The (6,11-dihydro-5H-pyrido[2,3-b][1,5]benzodiazepin-6-yl)-(4-fluoro-2-trifluoromethyl-phenyl)-methanone of Example 4, Step B (0.75 g, 1.94 mmol) was added in one portion and the mixture was placed in an oil bath (preheated at 130° C.) overnight. After cooling, the mixture was partitioned between water and ethyl acetate. The organic extracts were dried over sodium sulfate, and evaporated to dryness in vacuo. The residue was crystallized from ethanol to yield the title compound (0.57 g) as an off-white solid, m.p. 127–129° C.

NMR (DMSO-$d_6$, 400 MHz): δ4.19 and 5.46 (dd, 2H), 6.54 (m, 1H), 6.70 (m, 1H), 6.80 (m, 1H), 7.02 (m, 1H), 7.07 (m, 1H), 7.29 (m, 1H), 7.61 (m, 1H), 8.00 (m, 1H), 8.05–8.16 (m, 2H), 8.84 (m, 1H), 9.63 (s, 1H, NH)

MS (EI, m/z): 503 [M]$^+$

Anal. Calc'd for $C_{24}H_{15}F_6N_5O$: C 57.26, H 3.00, N 13.91. Found: C 57.07, H 2.97, N 13.58.

Step B. [2-(Trifluoromethyl)-4-(3-trifluoromethyl)-1H-pyrazol-1-yl)-phenyl-(6,11-dihydro-5H-pyrido[2,3-b][1,5]benzodiazepin-6-yl]-methanone-1-oxide Prepared by treatment of [2-(trifluoromethyl)-4-(3-trifluoromethyl)-1H-pyrazol-1-yl)-phenyl]-(6,11-dihydro-5H-pyrido[2,3-b][1,5]benzodiazepin-6-yl)-methanone of Step A with meta-chloro perbenzoic acid in the manner of Example 4, Step D.

EXAMPLE 8

[2-Fluoro-4-(3-methyl-1H-pyrazol-1-yl)-phenyl]-(6,11-dihydro-5H-pyrido[2,3-b][1,5]benzodiazepin-6-yl)-methanone-1-oxide Step A. 2,4-Difluoro benzoylchloride A suspension of 2,4-difluorobenzoic acid (3.6 g, 22.8 mmol) in dichloromethane (40 mL) containing a few drops of dimethylformamide was treated dropwise under nitrogen with oxalyl chloride (2.4 mL, 27.5 mmol). After gas evolution subsided, the reaction mixture was refluxed for an additional 15 minutes, and then the solution was evaporated to dryness in vacuo. The crude acid chloride was used as such in the next step.

Step B. (2,4-Difluoro-phenyl)-(6,11-dihydro-5H-pyrido[2,3-b][1,5]benzodiazepin-6-yl)-methanone To a solution of 6,11-dihydro-5H-pyrido[2,3-b][1,5]benzodiazepine of Example 1, Step B (3.0 g, 15.2 mmol) in dimethylformamide (35 mL) under nitrogen was added potassium carbonate (6.3 g, 45.6 mmol) followed by a solution of the crude 2,4-difluorobenzoylchloride of Step A (22.8 mmol) in dimethylformamide (15 mL). After stirring at room temperature for 20 minutes, the reaction mixture was washed with water and stirred to give a solid which was collected by filtration. The solid was dissolved in chloroform and washed with 1 N sodium hydroxide and brine. The organic phase was dried over sodium sulfate and evaporated to dryness. The crude material was dissolved in dichloromethane and absorbed onto a silica Merck-60 flash column. Elution with 20% ethyl acetate in hexane provided the title compound (2.6 g) as a white foam which crystallized by sonication from hexane-ethanol, m.p. 161–163° C.

NMR (DMSO-$d_6$, 400 MHz): δ4.12–5.46 (dd, 2H), 6.52 (m, 1H), 6.67 (m, 1H), 6.76 (m, 1H), 6.98–7.07 (m, 3H), 7.26 (m, 1H), 7.35 (m, 1H), 7.57 (m, 1H), 8.10 (m, 1H), 9.56 (s, 1H)

MS (EI, m/z): 337 [M]$^+$

Anal. Calc'd for $C_{19}H_{13}F_2N_3O$: C 67.65; H 3.88; N 12.46. Found: C 67.30; H 3.98; N 12.10.

Step C. [2-Fluoro-4-(3-methyl-1H-pyrazol-1-yl)-phenyl]-(6,11-dihydro-5H-pyrido[2,3-b][1,5]benzodiazepin-6-yl)-methanone 0.19 hydrate Sodium hydride (60% suspension in oil, 0.48 g, 12.0 mmol) was washed with hexane, dried under nitrogen and resuspended in dry dimethylformamide (60 mL). Neat 3-methylpyrazole (0.48 mL, 6.0 mmol) was added. Stirring was continued until the gas evolution subsided. The (2,4-difluoro-phenyl)-(6,11-dihydro-1H-pyrido[2,3-b][1,5]benzodiazepin-10-yl)-methanone of Step B (2.0 g, 5.9 mmol) was added in one portion to the clear solution. The mixture was placed in an oil bath (preheated at 130° C.) for 1 hour, cooled and partitioned between water and ethyl acetate. The organic extracts were dried over sodium sulfate and evaporated to dryness. The crude material was dissolved in dichloromethane and absorbed onto a silica Merck-60 flash column. Elution with hexane-ethyl acetate (gradient from 9:1 to 1:1) provided the title compound along with the more polar 4-fluoro regioisomer of Example 9. The title compound (0.30 g) was obtained as a foam which crystallized by sonication from hexane-ethanol, m.p. 122–125° C.

NMR (DMSO-$d_6$, 400 MHz): δ2.21 (s, 3H), 4.13 and 5.48 (dd, 2H), 6.32 (m, 1H), 6.51 (m, 1H), 6.70 (m, 1H), 6.77 (m, 1H), 7.01 (m, 1H), 7.27 (m, 1H), 7.35 (m, 1H), 7.41 (m, 1H), 7.53–7.59 (m, 2H), 8.10 (m, 1H), 8.35 (m, 1H), 9.57 (s, 1H)

MS (EI, m/z): 399 $[M]^+$

Anal. Calc'd for $C_{23}H_{18}FN_5O+0.19\ H_2O$: C 68.57, H 4.60, N 17.38. Found: C 68.53, H 4.68, N 17.56.

Step D. [2-Fluoro-4-(3-methyl-1H-pyrazol-1-yl)-phenyl]-(6,11-dihydro-5H-pyrido[2,3-b][1,5]benzodiazepin-6-yl)-methanone-1-oxide Prepared by treatment of [2-fluoro-4-(3-methyl-1H-pyrazol-1-yl)-phenyl]-(6,11-dihydro-5H-pyrido[2,3-b][1,5]benzodiazepin-6-yl)-methanone of Step C with meta-chloro perbenzoic acid in the manner of Example 1, Step F.

EXAMPLE 9

[4-Fluoro-2-(3-methyl-1H-pyrazol-1-yl)-phenyl]-(6,11-dihydro-5H-pyrido [2,3-b][1,5]benzodiazepin-6-yl)-methanone-1-oxide Step A. [4-Fluoro-2-(3-methyl-1H-pyrazol-1-yl)-phenyl]-(6,11-dihydro-5H-pyrido[2,3-b][1,5]benzodiazepin-6-yl)-methanone solvate with 0.20 ethanol The title product was obtained along with its 2-fluoro regioisomer as described in Example 8. The material was further purified by preparative HPLC (Waters silica cartridge, 55:45 hexane-ethyl acetate as the eluant, flow rate 150 mL/min, detection at 254 nm) to give the pure title compound (0.25 g) as a foam which crystallized by sonication from hexane-ethanol, m.p. 180–181° C.

MS (EI, m/z): 399 $[M]^+$

Anal. Calc'd for $C_{23}H_{18}FN_5O+0.20\ C_2H_6O$: C 68.78, H 4.74, N 17.14. Found: C 68.67, H 4.76, N 16.97.

Step B. [4-Fluoro-2-(3-methyl-1H-pyrazol-1-yl)-phenyl]-(6,11-dihydro-5H-pyrido[2,3-b][1,5]benzodiazepin-6-yl)-methanone-1-oxide Prepared by treatment of [4-fluoro-2-(3-methyl-1H-pyrazol-1-yl)-phenyl]-(6,11-dihydro-5H-pyrido[2,3-b][1,5]benzodiazepin-6-yl)-methanone of Step A with meta-chloro perbenzoic acid in the manner of Example 1, Step F.

EXAMPLE 10

[2-Methyl-5-(3-methyl-1H-pyrazol-1-yl)-phenyl]-(6,11-dihydro-5H-pyrido[2,3-b][1,5]benzodiazepin-6-yl)-methanone-1-oxide Step A. 5-Fluoro-2-methyl benzoylchloride A suspension of 5-fluoro-2-methyl benzoic acid (2.31 g, 15.0 mmol) in dichloromethane (30 mL) containing a few drops of dimethylformamide was treated dropwise under nitrogen with oxalyl chloride (1.6 mL, 18.3 mmol). After gas evolution subsided, the reaction mixture was refluxed for an additional 10 minutes, and then evaporated to dryness. The crude acid chloride was used as such in the next step.

Step B. [5-Fluoro-2-(methyl)-phenyl]-(6,11-dihydro-5H-pyrido[2,3-b][1,5]benzodiazepin-6-yl)-methanone To a solution of 6,11-dihydro-5H-pyrido[2,3-b][1,5]benzodiazepine of Example 1, Step B (2.0 g, 10.1 mmol) in dimethylformamide (15 mL) under nitrogen was added potassium carbonate (4.1 g, 29.7 mmol). The mixture was treated dropwise with a solution of crude 5-fluoro-2-methyl benzoyl chloride of Step A (15.0 mmol) in dimethylformamide (10 mL). After stirring at room temperature for 15 minutes, the mixture was diluted with water and stirred to give a solid mass which was collected by filtration. The solid was dissolved in chloroform and washed with 1 N sodium hydroxide and brine. The organic layer was dried over sodium sulfate and evaporated to dryness to give a purple oil. The crude material was dissolved in dichloromethane and absorbed onto a silica Merck-60 flash column. Elution with 20% ethyl acetate in hexane provided 1.88 g of the title product as a foam which was crystallized by sonication from ethanol-hexane, m.p. 138–140° C.

NMR (DMSO-$d_6$, 400 MHz): δ1.95 (s, 3H), 4.11 and 5.46 (dd, 2H), 6.53 (m, 1H), 6.75–6.80 (m, 2H), 6.81–7.06 (m, 4H), 7.24 (m, 1H), 7.60 (m, 1H), 8.11 (m, 1H), 9.57 (s, 1H)

MS (EI, m/z): 333 $[M]^+$

Anal. Calc'd for $C_{20}H_6FN_3O$: C 72.06, H 4.84, N 12.60. Found: C 71.88, H 4.78, N 12.67.

Step C. [2-Methyl-5-(3-methyl-1H-pyrazol-1-yl)-phenyl]-(6,11-dihydro-5H-pyrido[2,3-b][1,5]benzodiazepin-6-yl)-methanone Sodium hydride (60% suspension in oil, 0.25 g, 6.25 mmol) was washed with hexane, dried under nitrogen and resuspended in dry dimethylformamide (10 mL). Neat 3-methylpyrazole (0.28 mL, 3.5 mmol) was added in one portion at ambient temperature. Stirring was continued until the gas evolution subsided. The (5-fluoro-2-(methyl)-phenyl)-(6,11-dihydro-5H-pyrido[2,3-b][1,5]benzodiazepin-6-yl)-methanone of Step B (0.75 g, 1.94 mmol) was added in one portion to the clear solution. The mixture was heated to reflux for 26 hours, cooled and partitioned between water and ethyl acetate. The organic extracts were dried over sodium sulfate and evaporated to dryness. The residue was dissolved in dichloromethane and absorbed onto a silica Merck-60 flash column. Elution with hexane-ethyl acetate (gradient from 8:2 to 7:3) provided the title product (0.55 g) as a pale yellow foam which was crystallized by sonication from hexane-ethanol, m.p. 209–210° C.

NMR (DMSO-$d_6$, 400 MHz): δ1.94 (s, 3H), 2.23 (s, 3H), 4.13 and 5.49 (dd, 2H), 6.28 (m, 1H), 6.50 (m, 1H), 6.78 (m, 2H), 6.97 (m, 1H), 7.07 (m, 1H), 7.24 (m 7.51 (m, 1H), 7.62 (m, 1H), 8.11 (m, 1H), 8.19 (m, 1H), 9.60 (s, 1H)

MS (EI, m/z): 395 $[M]^+$

Anal. Calc'd for $C_{24}H_{21}N_5O$: C 72.89, H 5.35, N 17.71. Found: C 72.57, H 5.49, N 17.46.

Step D. [2-Methyl-5-(3-methyl-1H-pyrazol-1-yl)-phenyl]-(6,11-dihydro-5H-pyrido[2,3-b][1,5]benzodiazepin-6-yl)-methanone-1-oxide Prepared by treatment of [2-Methyl-5-(3-methyl-1H-pyrazol-1-yl)-phenyl]-(6,11-dihydro-5H-pyrido[2,3-b][1,5]

benzodiazepin-6-yl)-methanone of Step C with meta-chloro perbenzoic acid in the manner of Example 1, Step F.

EXAMPLE 11

[4-(3-tert-Butyl-1H-pyrazol-1-yl)-2-(trifluoromethyl)-phenyl]-(6,11-dihydro-5H-pyrido[2,3-b][1,5]benzodiazepin-6-yl)-methanone-1-oxide Step A. [4-(3-tert-Butyl-1H-pyrazol-1-yl)-2-(trifluoromethyl)-phenyl]-(6,11-dihydro-5H-pyrido[2,3-b][1,5]benzodiazepin-6-yl)-methanone Sodium hydride (60% suspension in oil, 0.12 g, 3.0 mmol) was washed with hexane, dried under nitrogen and resuspended in dry dimethylformamide (10 mL). 3-tert-butylpyrazole (0.20 g, 1.6 mmol) was added in one portion at ambient temperature, and the stirring was continued until the gas evolution subsided. The (6,11-dihydro-5H-pyrido[2,3-b][1,5]benzodiazepin-6-yl)-[4-fluoro-2-trifluoromethyl-phenyl]-methanone of Example 4, Step B (0.50 g, 1.3 mmol) was added in one portion to the clear solution. The mixture was placed in an oil bath (preheated at 130° C.) for 30 minutes and then heated at reflux for 5 hours. After cooling, the mixture was partitioned between water and ethyl acetate. The organic extracts were dried over sodium sulfate and evaporated to dryness. The crude residue was dissolved in dichloromethane and absorbed onto a silica Merck-60 flash column. Elution with 25% ethyl acetate in hexane provided the title product (0.23 g) as a foam which crystallized by trituration with hexane-ether, m.p. 136–140° C.

NMR (DMSO-$d_6$, 400 MHz): $\delta$1.26 (s, 9H), 4.17 and 5.45 (dd, 2H), 6.47 (m, 1H), 6.54 (m, 1H), 6.68 (m, 1H), 6.80 (m, 1H), 7.00 (m, 1H), 7.28 (m, 1H), 7.60 (m, 1H), 7.87 (m, 1H), 8.04 (m, 1H), 8.13 (m, 1H), 8.47 (m, 1H), 9.62 (s, 1H)

MS (EI, m/z): 491 [M]$^+$

Anal. Calc'd for $C_{72}H_{24}F_3N_5O$: C 65.98, H 4.92, N 14.25. Found: C 65.75, H 4.92, N 13.95.

Step B. [4-(3-tert-Butyl-1H-pyrazol-1-yl)-2-(trifluoromethyl)-phenyl]-(6,11-dihydro-1H-pyrido[2,3-b][1,5]benzodiazepin-6-yl)-methanone 1-oxide Prepared by treatment of [4-(3-tert-butyl-1H-pyrazol-1-yl)-2-(trifluoromethyl)-phenyl]-(6,11-dihydro-5H-pyrido[2,3-b][1,5]benzodiazepin-6-yl)-methanone of Step A with meta-chloro perbenzoic acid in the manner of Example 1, Step F.

EXAMPLE 12

{2-Chloro-4-[3-(trifluoromethyl)-1H-pyrazol-1-yl]-phenyl]-(6,11-dihydro-5H-pyrido[2,3-b][1,5]benzodiazepin-6-yl)-methanone 1-oxide Step A. {2-Chloro-4-[3-(trifluoromethyl)-1H-pyrazol-1-yl]-phenyl}-(6,11-dihydro-5H-pyrido[2,3-b][1,5]benzodiazepin-6-yl)-methanone Sodium hydride (60% suspension in oil, 0.195 g) was washed with hexane, dried under nitrogen and resuspended in dry dimethylformamide (10 mL). 3-trifluoromethyl pyrazole (0.364 g) was added dropwise at 0° C. After the gas evolution subsided the solution was brought to room temperature. The (2-chloro-4-fluoro-phenyl)-(6,11-dihydro-5H-pyrido[2,3-b][1,5]benzodiazepin-6-yl)-methanone of Example 1, Step D (0.787 g, 2.23 mmol) was added in one portion and the mixture was placed in an oil bath (preheated at 130° C.) for 4.5 hours. The mixture was cooled and partitioned between saturated aqueous ammonium chloride and ethyl acetate. The organic extracts were dried over sodium sulfate and evaporated to dryness in vacuo. The residue was dissolved in dichloromethane and absorbed onto a silica Merck-60 flash column. Elution with hexane-ethyl acetate (gradient from 95:5 to 3:2) provided the desired product (0.727 g) which crystallized by sonication from hexane-ethanol as an off-white solid, m.p. 183–185° C.

NMR (DMSO-$d_6$, 400 MHz): $\delta$4.16 and 5.45 (dd, 2H), 6.52 (m, 1H), 6.78 (m, 2H), 7.01 (m, 2H), 7.04 (m, 1H), 7.26 (m, 1H), 7.61 (m, 1H), 7.74–7.84 (2m, 2H), 8.12 (m, 1H), 8.74 (m, 1H), 9.58 (s, 1H)

MS (EI, m/z): 469/471 [M]$^+$, 273/275, 196

Anal. Calc'd for $C_{23}H_{15}ClF_3N_5O$: C 58.80, H 3.22, N, 14.91. Found: C 58.67, H 3.14, N 14.83.

Step B. {2-Chloro-4-[3-(trifluoromethyl)-1H-pyrazol-1-yl]-phenyl]-(6,11-dihydro-5H-pyrido[2,3-b][1,5]benzodiazepin-6-yl)-methanone-1-oxide Prepared by treatment of { 2-chloro-4-[3-(trifluoromethyl)-1H-pyrazol-1-yl}-phenyl]-(6,11-dihydro-5H-pyrido[2,3-b][1,5]benzodiazepin-6-yl)-methanone of Step A in the manner of Example 1, Step F.

EXAMPLE 13

[2-Chloro-4-(1-methyl-1-H-pyrazol-3-yl)-phenyl]-(6,11-dihydro-5H-pyrido[2,3-b][1,5]benzodiazepin-6-yl)-methanone-1-oxide Step A. 2-Chloro-4-(3-dimethylaminopropyn-1-yl)-benzoic acid methyl ester Under an atmosphere of nitrogen, a mixture of 4-bromo-2-chlorobenzoic acid methyl ester (25.13 g, 101 mmol), 1-dimethylamino-2-propyne (16 mL, 150 mmol), bis(triphenylphosphine)palladium(II) chloride (1.0 g) and copper (I) iodide (0.15 g) in 100 mL of triethylamine was heated at 60° C. for 2 hours. The cooled reaction mixture was filtered through Solka floc and the cake was washed with ethyl acetate. The filtrate was partitioned between ethyl acetate and dilute aqueous sodium thiosulfate. The organic layer was washed with water, brine and dried over sodium sulfate. The dark solution was filtered through a plug of Merck-60 silica gel and the filtrate was concentrated in vacuo to give the title compound (23.8 g) as an orange oil, which was used as such in the next step.

NMR (DMSO-$d_6$, 300 MHz): $\delta$2.25 (s, 6H), 3.475 (s, 2H), 3.84 (s, 3H), 7.5 (dd, 1H), 7.62 (s, 1H), 7.8 (d, 1H).

Step B. 2-Chloro-4-(3-dimethylamino-2-propen-1-yl)-benzoic acid methyl ester

Under an atmosphere of nitrogen, purified meta-chloroperbenzoic acid (16.0 g, 93 mmol) was added portionwise to a stirred solution of 2-chloro-4-(3-dimethylaminopropyn-1-yl)-benzoic acid methyl ester of Step A (23.5 g, 93.4 mmol) in 200 mL of dichloromethane at −10° C. After the addition was complete, the solution was stirred at reduced temperature for 30 minutes and then filtered through a column of basic alumina (400 g, Brockman activity I) packed with dichloromethanemethanol (9:1, v/v). The intermediate N-oxide was eluted with the above solvent system. The dichloromethane was then carefully replaced with methanol by evaporation at or below room temperature, taking care that the mixture is never allowed to evaporate to dryness. The methanolic solution was heated at 60° C. overnight, and then was concentrated in vacuo. The residue was purified by flash chromatography (on Merck-60 silica gel, hexane-ethyl acetate 1:1) to give 12.1 g of a slightly impure product. Trituration with diethyl ether provided the pure title compound (6.15 g) as an orange solid.

NMR (DMSO-$d_6$, 300 MHz): δ2.98 (s, 3H), 3.2 (s, 3H), 3.83 (s, 3H), 5.85 (d, 1H), 7.75–8.0 (m, 4H).

Step C. 2-Chloro-4-(1H-pyrazol-3-yl)-benzoic acid methyl ester

A solution of 2-chloro-4-(3-dimethylamino-2-propen-1-yl)-benzoic acid methyl ester of Step B (6.13 g, 22.9 mmol) and anhydrous hydrazine (1.44 mL, 45.8 mmol) in 15 mL of glacial acetic acid was heated at 90° C. for 30 minutes. The reaction mixture was concentrated in vacuo and the residue partitioned between ethyl acetate and water. The organic layer was washed with water and brine and dried over sodium sulfate. The solvent was evaporated and the residual solid triturated with diethyl ether-hexane to give the title compound (5.1 g) as an orange solid.

NMR (DMSO-$d_6$, 300 MHz): δ3.85 (s, 3H), 6.9 (d, 1H), 7.9 (m, 3H), 8.0 (d, 1H), 13.15 (broad, 1H).

Step D. 2-Chloro-4-(1-methyl-1H-pyrazol-3-yl)-benzoic acid methyl ester

Under an atmosphere of nitrogen, a solution of 2-chloro-4-(1H-pyrazol-3-yl)-benzoic acid methyl ester of Step C (5.0 g, 21.1 mmol) in 50 mL of dry dimethylformamide was added dropwise to a stirred mixture of hexane washed sodium hydride (0.51 g, 21.1 mmol) in 5 mL of dry dimethylformamide. The mixture was stirred at ambient temperature for 30 minutes, methyl iodide (2.7 mL, 42.2 mmol) was added to the resulting solution and the stirring was continued overnight at room temperature. The reaction mixture was poured into water and extracted with ethyl acetate. The organic layer was washed with water, brine and dried over sodium sulfate. Removal of solvent in vacuo afforded 4.8 g of an orange oil. Flash chromatography of the crude material (on silica gel Merck-60, hexane-ethyl acetate, 4:1) provided 2.9 g of the desired 1-methylpyrazole regioisomer.

NMR (DMSO-$d_6$, 300 MHz): δ3.84 (s, 3H), 3.9 (s, 3H), 6.875 (d, 1H), 7.8 (d, 1H), 7.85 (s, 2H), 7.95 (s, 1H).

Step E. 2-Chloro-4-(1-methyl-1H-pyrazol-3-yl)-benzoic acid

A solution of 2-chloro-4-(1-methyl-1H-pyrazol-3-yl)-benzoic acid methyl ester of Step D (2.9 g, 11.6 mmol) in 20 mL of methanol containing 5 mL of 2.5 N sodium hydroxide was stirred at ambient temperature overnight. An additional 2.0 mL of 2.5 N sodium hydroxide were added and the solution was gently heated for 30 minutes. The reaction mixture was concentrated in vacuo, diluted with water, and acidified with 2N hydrochloric acid. The precipitate was collected and thoroughly dried to give 2.55 g of the title compound.

NMR (DMSO-$d_6$, 300 MHz): δ3.9 (s, 3H), 6.85 (d, 1H), 7.82 (m, 3H), 7.95 (s, 1H), 13.3 (broad, 1H).

Step F. [2-Chloro-4-(1-methyl-1H-pyrazol-3-yl)-phenyl]-(6,11-dihydro-5H-pyrido[2,3-b][1,5]benzodiazepin-6-yl)-methanone Under anhydrous conditions a solution of 2-chloro-4-(1-methyl-1H-pyrazol-3-yl)-benzoic acid of Step E (2.1 g, 8.88 mmol) and triethylamine (1.3 mL, 9.2 mmol) in 75 mL of dichloromethane was treated in one portion with 2,4,6-trichlorobenzoyl chloride (1.48 mL, 9.2 mmol) and stirred at ambient temperature for 2 hours. To the solution was added the 6,11-dihydro-5H-pyrido[2,3-b][1,5]benzodiazepine of Example 1, Step B (1.74 g, 8.9 mmol) followed by 4-dimethylaminopyridine (1.1 g, 8.9 mmol) and stirring was continued for 18 hours. The reaction mixture was washed sequentially with saturated sodium bicarbonate and brine. After drying over sodium sulfate, the solution was concentrated to small volume and absorbed onto silica Merck-60. Elution with ethyl acetate-hexane (gradient from 4:3 to 2:1) gave the pure title compound as a syrup which crystallized from diethylether. The white solid (0.78 g) melted at 196–197° C.

NMR (DMSO-$d_6$, 400 Mhz): δ3.831 (s, 3H), 4.13 (d, 1H), 5.43 (d, 1H), 6.497 (t, 1H), 6.71 (d, 1H), 6.76 (m, 2H), 6.97 (t, 1H), 7.24 (d, 1H), 7.6 (m, 3H), 7,705 (d, 1H), 8.10(dd, 1H), 9.544 (s, 1H).

MS (EI, m/z): 415/417 [M]$^+$, 219/221

Anal. Calc'd for $C_{23}H_{18}ClN_5O$: C 66.42, H 4.36, N 16.84. Found: C 66.20, H 4.49, N 16.59.

Step G. [2-Chloro-4-(1-methyl-1-H-pyrazol-3-yl)-phenyl]-(6,11-dihydro-5H-pyrido[2,3-b][1,5]benzodiazepin-10-yl)-methanone 1-oxide Prepared by treatment of [2-chloro-4-(1-methyl-1H-pyrazol-3-yl)-phenyl]-(6,11-dihydro-5H-pyrido[2,3-b][1,5]benzodiazepin-10-yl)-methanone of Step F with meta-chloro perbenzoic acid in the manner of Example 1, Step F.

EXAMPLE 14

[2-Chloro-4-(1-methyl-1H-pyrazol-3-yl)-phenyl]-(6,11-dihydro-5H-pyrido[2,3-b][1,5]benzodiazepin-6-yl)-methanone Under anhydrous conditions a mixture of the 2-chloro-4-(1-methyl-1H-pyrazol-3-yl)-benzoic acid of Example 13, Step E (1.9 g, 8.05 mmol) and oxalyl chloride (0.79 mL, 9.0 mmol) in 20 mL of dichloromethane containing a catalytic amount of dimethylformamide was stirred at ambient temperature for 1 hour. The solvent was evaporated and the solid acid chloride was dissolved in 5 mL of dimethylformamide and added directly to a mixture of 6,11-dihydro-5H-pyrido[2,3-b][1,5]benzodiazepine of Example 1, Step B (1.59 g, 8.05 mmol) and potassium carbonate (1.25 g, 9.0 mmol). After stirring for 2 hours at ambient temperature the reaction mixture was partitioned between ethyl acetate and water. The organic phase was washed with water and brine, dried over sodium sulfate, and concentrated to small volume. Flash chromatography of the residue (on silica Merck 60, ethyl acetate-hexane, gradient from 4:3 to 2:1) gave the product as a syrup which crystallized from diethyl ether (1.8 g, 61% yield1) as a white solid, m.p. 196–197° C. Another recrystallization from ethanol-diethyl ether provided a higher melting polymorph, m.p. 202° C. as determined by differential scanning calorimetry.

MS (+FAB, m/z): 416/418 (M+H)$^+$.

Anal. Calc'd for $C_{23}H_{18}ClN_5O$: C 66.42, H 4.36, N 16.84. Found: C 66.20, H 4.42, N 16.80.

EXAMPLE 15

[2-Chloro-4-(3-methyl-1H-pyrazol-1-yl)-phenyl]-(6,11-dihydro-5H-pyrido[2,3-b][1,5]benzodiazepin-6-yl)-methanone

Step A. 2-Chloro-4-(3-methyl-1H-pyrazol-1-yl)-benzoic acid methyl ester

Under anhydrous conditions a stirred suspension of hexane washed potassium hydride (0.424 g, 10.6 mmol) in 5 mL of dimethylformamide was treated in one portion with 3-methyl pyrazole (0.85 mL, 10.6 mmol). After the gas evolution ceased, 2-chloro-4-fluorobenzoic acid methyl ester (2.0 g, 10.6 mmol) was added to the clear solution. The mixture was heated at 130° C. for 15 minutes, cooled, and partitioned between ethyl acetate and brine. The organic layer was washed with water and brine, and dried over sodium sulfate. Removal of solvent afforded 2.2 g of a yellow oil consisting of a mixture of 3-methyl and 5-methylpyrazole regioisomers. In addition, about 20% of the acid derived from hydrolysis of the ester was detected by analysis of the NMR spectrum of the crude product. The desired 3-methylpyrazole regioisomer was separated from the 5-methyl isomer of Example 16 by flash chromatography (on silica Merck-60, dichloromethane-hexane 2:1) and was isolated as a white solid (1.55 g).

NMR (DMSO-$d_6$, 400 MHz): δ2.26 (s, 3H), 3.84 (s, 3H), 6.40 (d, 1H), 7.86 (dd, 1H), 7.93 (d, 1H), 8.00 (s, 1H), 8.53 (d, 1H).

MS (EI, m/z): 250/252 [M]$^+$, 219

Step B. 2-Chloro-4-(3-methyl-1H-pyrazol-1-yl)-benzoic acid

A solution of 2-chloro-4-(3-methyl-1H-pyrazol-1-yl)-benzoic acid methyl ester of Step A (1.42 g, 5.6 mmol) in 20 mL of tetrahydrofuran containing 6 mL of 1 M aqueous lithium hydroxide was stirred overnight at ambient temperature. The reaction mixture was partitioned between ethyl acetate and 1 N hydrochloric acid. The organic layer was washed with water and brine, and dried over sodium sulfate. Evaporation of the solvent afforded the title compound (1.05 g), m.p. 192–193° C.

NMR (DMSO-$d_6$, 400 MHz): δ2.27 (s, 3H), 6.40 (d, 1H), 7.84 (dd, 1H), 7.92 (d, 1H), 8.00 (s, 1H), 8.53 (d, 1H), 13.32 (broad, 1H).

MS (EI, m/z): 236/238 [M]$^+$, 219

Anal. Calc'd for $C_{11}H_9ClN_2O_2$: C, 55.83, H 3.83, N 11.84. Found: C 55.79, H 3.98, N 11.73.

Step C. [2-Chloro-4-(3-methyl-1H-pyrazol-1-yl)-phenyl]-(6,11-dihydro-5H-pyrido[2,3-b][1,5]benzodiazepin-6-yl)-methanone In the manner of Example 5, Step D, employing 2-chloro-4-(3-methyl-1H-pyrazol-1-yl)-benzoic acid of Step B (0.971 g, 4.1 mmol), triethylamine (0.57 mL, 4.1 mmol), 2,4,6-trichlorobenzoylchloride (0.63 mL, 4.0 mmol), 6,11-dihydro-5H-pyrido[2,3-b][1,5]benzodiazepine of Example 1, Step B (0.67 g, 3.4 mmol) and 4-dimethylamino pyridine (0,42 g, 3.4 mmol) in dichloromethane (20 mL), was obtained a compound identical to that of Example 1, Step E.

EXAMPLE 16

2-Chloro-4-(5-methyl-1H-pyrazol-1-yl)-benzoic acid methyl ester.

The title compound was prepared as described in Example 15, Step A and separated from the 3-methylpyrazole isomer of Example 15, Step A by flash chromatography (on silica Merck-60, eluant: dichloromethane). It was obtained as a white solid (0.20 g).

NMR (DMSO-$d_6$, 400 MHz): δ2.42 (s, 3H), 3.87 (s, 3H), 6.33 (s, 1H), 7.65 (m, 2H), 7.79 (s, 1H), 7.95 (d, 1H).

MS (EI, m/z): 250/252 [M]$^+$, 219.

EXAMPLE 17

(2-Chloro-4-fluorophenyl)-(6,11-dihydro-5H-pyrido[2,3-b][1,5]benzodiazepin-6-yl-methanone To a solution of 6,11-dihydro-5H-pyrido[2,3-b][1,5]benzodiazepine of Example 1, Step B (0.100 g, 0.51 mmol) in tetrahydrofuran (5 mL) was added 4-dimethylamino pyridine (0.190 g, 1.55 mmol) followed by 2-chloro-4-fluorobenzoylchloride (0.100 mL, 0.76 mmol). The mixture was stirred overnight at room temperature and then evaporated to dryness. The residue was partitioned between aqueous saturated ammonium chloride and dichloromethane. The organic layer was dried over sodium sulfate and evaporated to dryness to provide the title compound identical to the material described in Example 1, Step D.

EXAMPLE 18

[2-Chloro-4-(5-methyl-1H-[1,2,4]triazol-3-yl)-phenyl]-(6,11-dihydro-5H-pyrido[2,3-b][1,5]benzodiazepin-6-yl)-methanone-1-oxide

Step A. 2-Chloro-terephthalamic acid methyl ester

A mixture of 2-chloro-4-cyano benzoic acid methyl ester (12.4 g, 63.4 mmol) and potassium carbonate (1.3 g, 9.4 mmol) in dimethylsulfoxide (40 mL) was treated dropwise under cooling with 30% hydrogen peroxide (7.6 mL). The mixture was allowed to warm to room temperature and stirred overnight. The solution was quenched with water and the resulting precipitate collected by filtration. The crude material was dissolved in dichloromethane and absorbed on a silica gel Merck-60 flash column. Elution with a dichloromethane-methanol gradient (from 98:2 to 90:10) provided the title compound (10 g) as a white solid, m.p. 154–156° C.

NMR (DMSO-$d_6$, 400 MHz): δ3.87 (s, 3H), 7.67 (s, 1H), 7.86–7.91 (m, 2H), 8.00–8.01 (m, 1H), 8.20 (s, 1H)

MS (EI, m/z): 213 [M]$^+$

Anal. Calc'd for $C_9H_8ClNO_3$: C 50.60, H 3.77, N 6.56. Found: C 50.36, H 3.66, N 6.44.

Step B. 2-Chloro N-(1-dimethylaminoethylidene)-terephthalamic acid methyl ester A mixture of 2-chloro-terephthalamic acid methyl ester of Step A (1.02 g, 4.8 mmol) and N,N-dimethylacetamide dimethyl acetal (3.5 mL, 23.9 mmol) was heated at 90° C. for 30 minutes under nitrogen. The solution was cooled, and excess reagent was removed under high vacuum to provide a brown oil which was used as such in the next step.

NMR (DMSO-$d_6$, 400 MHz): δ2.29 (s, 3H), 3.14 (s, 3H), 3.16 (s, 3H), 3.87 (s, 3H), 7.83–7.85 (m, 1H), 8.00–8.06 (m, 2H)

MS (EI, m/z): 282 [M]$^+$

Step C. 2-Chloro-4-(5-methyl-1H-[1,2,4]triazol-3-yl)-benzoic acid methyl ester Anhydrous hydrazine (0.30 mL, 9.6 mmol) was added via syringe to a solution of the intermediate of Step B (4.8 mmol) in glacial acetic acid (6 mL) under a nitrogen atmosphere. The reaction was heated at 90° C. for 30 minutes, then cooled and concentrated in vacuo to a light brown solid. The solid was redissolved in aqueous methanol and the solution neutralized with saturated aqueous sodium bicarbonate. The mixture was extracted with dichloromethane and ethyl actate, the extracts were combined and dried over sodium sulfate. Evaporation of the solvents yielded a solid which was triturated with ether to provide the title product (0.81 g) as an off-white solid, m.p. 196–198° C.

NMR (DMSO-$d_6$, 400 MHz): δ2.41 (s, 3H), 3.86 (s, 3H), 7.90–8.05 (m, 3H), 13.94 (s, 1H)

MS (EI, m/z): 251 [M]+

Anal. Calc'd for $C_{11}H_{10}ClN_3O_2$: C 52.50, H 4.01, N, 16.70. Found: C 52.68, H 3.83, N 16.50.

Step D. 2. Chloro-4-[1-(4-methoxy-benzyl)-5-methyl-1H-[1,2,4]triazol-3-yl]-benzoic acid methyl ester 0.03 solvate with dichloromethane Sodium hydride (60% suspension in oil, 0.30 g, 7.5 mmol) was washed with hexane and resuspended in dry dimethylformamide (20 mL) under a nitrogen atmosphere. The triazole intermediate of Step C (1.36 g, 5 mmol) was added and the mixture was stirred for one hour. p-Methoxybenzyl chloride (0.75 mL, 5.5 mmol) was added and after stirring for 3 hours, the reaction was quenched with water and extracted with ethyl acetate. The extracts were combined, dried over anhydrous sodium sulfate and concentrated in vacuo. The residue was dissolved in dichloromethane and absorbed on a silica Merck 60 flash column. Elution with 3% ethyl acetate in dichloromethane provided the title compound (1.23 g) as a white solid, m.p. 102–104° C.

NMR (DMSO-$d_6$, 400 MHz): $\delta$2.48 (s, 3H), 3.72 (s, 3H), 3.86 (s, 3H), 5.35 (s, 2H), 6.90–6.92 (m, 2H), 7.23–7.25 (m, 2H), 7.89–8.02 (m, 3H)

MS (EI, m/z): 371 [M]+

Anal. Calc'd for $C_{19}H_{18}ClN_3O_3+0.03\ CH_2CH_{12}$: C 61.05, H 4.86, N 11.22. Found: C 60.83, H4.96, N, 11.18.

Step E. 2-Chloro-4-[1-(4-methoxy-benzyl)-5-methyl-1H-[1,2,4]triazol-3-yl]-benzoic acid 0.10 hydrate 0.04 solvate with ethyl acetate A solution of the ester intermediate of Step D (1.6 g, 4.3 mmol) in methanol (15 mL) was treated with 2.5 N aqueous sodium hydroxide (3.5 mL, 8.8 mL) under a nitrogen atmosphere. The mixture was refluxed for two hours, cooled and concentrated in vacuo. The residue was partitioned between ethyl acetate and water. The aqueous layer was acidified with 1N aqueous HCl. The precipitate was collected by filtration to provide the title compound (1.25 g) as a white solid, m.p. 154–156° C.

NMR (DMSO-$d_6$, 400 MHz): $\delta$2.47 (s, 3H), 3.72 (s, 3H), 5.34 (s, 2H), 6.90–6.93 (m, 2H), 7.23–7.25 (m, 2H), 7.87–7.99 (m, 3H), 13.40 (s, 1H)

MS (EI, m/z): 357 [M]+

Anal. Calc'd for $C_{18}H_{16}ClN_3O_3+0.10\ H_2O+0.04\ C_4H_8O_2$: C 60.07, H 4.59, N 11.57. Found: C 59.75, H 4.41, N 11.43.

Step F. 2-Chloro-4-[1-(4-methoxy-benzyl)-5-methyl-1H-[1,2,4]triazol-3-yl]-benzoyl chloride A suspension of the acid of Step E (1 g, 2.8 mmol) in dichloromethane containing a few drops of dimethylformamide was treated dropwise under nitrogen with oxalyl chloride (0.30 mL, 3.4 mmol). After gas evolution subsided, the reaction mixture was refluxed for another 15 minutes and then evaporated to dryness in vacuo to provide the title compound which was used as such in the next step.

Step G. {2-Chloro-4-[1-(4-methoxy-benzyl)-5-methyl-1H-[1,2,4]triazol-3-yl]-phenyl}-(6,11-dihydro-5H-pyrido[2,3-b][1,5]benzodiazepin-6-yl)-methanone 0.06 dichloromethane solvate To a solution of 6,11-dihydro-5H-pyrido[2,3-b][1,5]benzodiazepine of Example 1, Step B (0.55 g, 2.8 mmol) in dimethylformamide (10 mL) under nitrogen was added solid potassium carbonate (0.39 g, 2.8 mmol). The mixture was treated dropwise with a solution of the crude acid chloride (2.8 mmol) of Step F in dimethylformamide (10 mL). After stirring at room temperature for 90 minutes, the reaction mixture was diluted with water and extracted with ethyl acetate. The organic extracts were combined and washed with 1N aqueous sodium hydroxide, dried over sodium sulfate and evaporated to dryness. The residue was dissolved in dichloromethane and absorbed on a column of flash silica Merck-60. Less polar impurities were eluted with 1:1 ethyl acetate-hexane. Further elution with 2% methanol in dichloromethane provided the title compound as a white solid (0.57 g), m.p. 218–221° C.

NMR (DMSO-$d_6$, 400 MHz): $\delta$2.42 (s, 3H), 3.71 (s, 3H), 4.14 and 5.44 (dd, 2H), 5.29 (s, 2H), 6.49 (m, 1H), 6.74–6.80 (m, 2H), 6.88–6.99 (m, 3H), 7.18–7.26 (m, 4H), 7.60 (m, 1H), 7.65–7.75 (m, 2H, ArH), 8.11 (m, 1H), 9.55 (s, 1H)

MS (ESI, m/z): 537 [M+H]+

Anal. Calc'd for $C_{30}H_{25}ClO_2+0.06\ CH_2C_2$: C 66.60, H 4.67, N 15.50. Found: C 66.24, H 4.85, N 15.23.

Step H. [2-Chloro-4-(5-methyl-1H-[1,2,4]triazol-3-yl)-phenyl]-(6,11-dihydro-5H-pyrido[2,3-b][1,5]benzodiazepin-6-yl)-methanone A solution of the triazole intermediate of Step G (0.54 g, 1.01 mmol) in trifluoroacetic acid (15 mL) was heated at reflux for seven days under a nitrogen atmosphere. The mixture was cooled and the trifluoroacetic acid removed in vacuo. The residue was dissolved in water and neutralized with saturated aqueous sodium bicarbonate. The mixture was extracted with ethyl acetate, the extracts were dried over sodium sulfate and concentrated in vacuo to give a pale yellow solid. The residue was dissolved in ethyl acetate-methanol and absorbed on a silica Merck-60 flash column. Elution with a solvent gradient (from 100% ethyl acetate to 5% methanol in ethyl acetate) provided the title compound (0.23 g, 54.6%) as a white solid, m. p.>270° C.

NMR (DMSO-$d_6$, 400 MHz): $\delta$2.36 (s, 3H), 4.15 and 5.45 (dd, 2H), 6.50 (m, 1H), 6.75–6.80 (m, 2H), 6.98 (m, 1H), 7.19–7.27 (m, 2H), 7.60 (m, 1H), 7.70–7.79 (m, 2H), 8.11 (m, 1H), 9.54 (s, 1H), 13.78 (s, 1H)

MS (+FAB, m/z): 417 [M+H]+

Anal. Calc'd for $C_{22}H_{17}ClN_6O$: C 63.39, H 4.11, N 20.16. Found: C 63.14, H 4.13, N, 19.90.

Step I. [2-Chloro-4-(5-methyl-1H-[1,2,4]triazol-3-yl)-phenyl]-(6,11-dihydro-5H-pyrido[2,3-b][1,5]benzodiazepin-6-yl)-methanone-1-oxide Prepared by treatment of [2-chloro-4-(5-methyl-1H-[1,2,4]triazol-3-yl)-phenyl]-(6,11-dihydro-5H-pyrido[2,3-b][1,5]benzodiazepin-6-yl)-methanone of Step H with meta-chloro perbenzoic acid in the manner of Example 1, Step F.

What is claimed:

1. A compound of the formula:

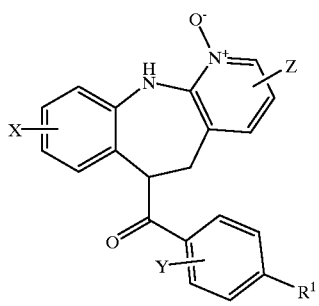

(I)

wherein:

R¹ is a group selected from

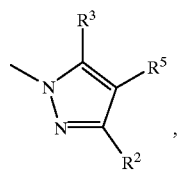 (a)

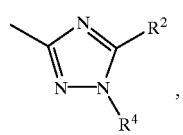 (c)

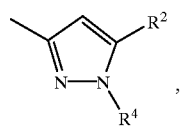 (d)

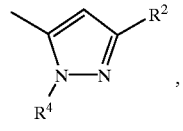 (e)

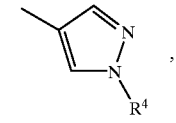 (f)

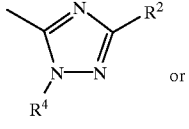 (g)   or

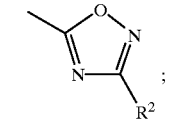 (i)

$R^2$, $R^3$ and $R^5$ are, independently, hydrogen, straight chain alkyl of 1 to 6 carbon atoms, branched chain alkyl of 3 to 7 carbon atoms, cycloalkyl of 3 to 7 carbon atoms, or perfluoroalkyl of 1 to 6 carbons;

$R^4$ is hydrogen, straight chain alkyl of 1 to 6 carbon atoms, branched chain alkyl of 3 to 7 carbon atoms, cycloalkyl of 3 to 7 carbon atoms, or optionally substituted aralkyl of 7 to 15 carbon atoms;

X and Y are, independently, hydrogen, straight chain alkyl of 1 to 6 carbon atoms, branched chain alkyl of 3 to 7 carbon atoms, cycloalkyl of 3 to 7 carbon atoms, alkoxyalkyl of 2 to 7 carbon atoms, halogen, straight chain or branched chain alkoxy of 1 to 6 carbons, $CF_3$, or perfluoroalkyl of 2 to 6 carbons;

and Z is hydrogen, or straight chain alkyl group of 1 to 6 carbon atoms, or branched chain alkyl of 3 to 7 carbon atoms;

or a pharmaceutically acceptable salt thereof.

2. A compound of claim 1 which is [2-chloro-4-(3-methyl-1H-pyrazol-1-yl)-phenyl]-(6,11-dihydro-5H-pyrido[2,3-b][1,5]benzodiazepin-6-yl)-methanone-1-oxide.

3. A compound of claim 1 which is [2-bromo-4-(3-methyl-1H-pyrazol-1-yl)-phenyl]-(6,11-dihydro-5H-pyrido[2,3-b][1,5]benzodiazepin-6-yl)-methanone-1-oxide.

4. A compound of claim 1 which is [4-(3-methyl-1H-pyrazol-1-yl)-2-(trifluoromethyl)-phenyl]-(6,11-dihydro-5H-pyrido[2,3-b][1,5]benzodiazepin-6-yl)-methanone-1-oxide.

5. A compound of claim 1 which is [2-Chloro-4-(5-methyl-1H-pyrazol-1-yl)-phenyl]-(6,11-dihydro-5H-pyrido[2,3-b][1,5]benzodiazepin-6-yl)-methanone-1-oxide.

6. A compound of claim 1 which is [4-(5-Methyl-1H-pyrazol-1-yl)-2-(trifluoromethyl)-phenyl]-(6,11-dihydro-5H-pyrido[2,3-b][1,5]benzodiazepin-6-yl)-methanone-1-oxide.

7. A compound of claim 1 which is {2-(Trifluoromethyl)-4-[3-(trifluoromethyl)-1H-pyrazol-1-yl]-phenyl}-(6,11-dihydro-5H-pyrido[2,3-b][1,5]benzodiazepin-6-yl)-methanone-1-oxide.

8. A compound of claim 1 which is [2-Fluoro-4-(3-methyl-1H-pyrazol-1-yl)-phenyl]-(6,11-dihydro-5H-pyrido[2,3-b][1,5]benzodiazepin-6-yl)-methanone-1-oxide.

9. A compound of claim 1 which is [4-Fluoro-2-(3-methyl-1H-pyrazol-1-yl)-phenyl]-(6,11-dihydro-5H-pyrido[2,3-b][1,5]benzodiazepin-6-yl)-methanone-1-oxide.

10. A compound of claim 1 which is [2-Methyl-5-(3-methyl-1H-pyrazol-1-yl)-phenyl]-(6,11-dihydro-5H-pyrido[2,3-b][1,5]benzodiazepin-6-yl)-methanone-1-oxide.

11. A compound of claim 1 which is [4-(3-tert-Butyl-1H-pyrazol-1-yl)-2-(trifluoromethyl)-phenyl]-(6,11-dihydro-5H-pyrido[2,3-b][1,5]benzodiazepin-6-yl)-methanone-1-oxide.

12. A compound of claim 1 which is [2-Chloro-4-(1-methyl-1H-pyrazol-3-yl)-phenyl]-(6,11-dihydro-5H-pyrido[2,3-b][1,5]benzodiazepin-6-yl)-methanone-1-oxide.

13. A compound of claim 1 which is [2-Chloro-4-(5-methyl-1H-[1,2,4]triazol-3-yl)-phenyl]-(6,11-dihydro-5H-pyrido[2,3-b][1,5]benzodiazepin-6-yl)-methanone 1-oxide.

14. A method of treating disorders which are remedied or alleviated by vasopressin agonist activity in a mammal, the method comprising administering to the mammal in need thereof a pharmaceutically effective amount of a compound of claim 1, or a pharmaceutically acceptable prodrug form thereof.

15. The method of claim 14 wherein the disorder which is remedied or alleviated by vasopressin agonist activity is selected from the group of diabetes insipidus, nocturnal enuresis, nocturia, urinary incontinence, bleeding and coagulation disorders, or temporary delay of urination.

16. A pharmaceutical composition comprising a pharmaceutically effective amount of a compound of claim 1 and a pharmaceutically acceptable carrier of excipient.

* * * * *